United States Patent
Na et al.

(10) Patent No.: US 11,712,418 B2
(45) Date of Patent: Aug. 1, 2023

(54) CHEMOEMBOLIZATION AGENTS

(71) Applicants: BRUIN BIOSCIENCES, INC., San Diego, CA (US); THE REGENTS OF THE UNIVERSITY OF CALIFORNIA, Oakland, CA (US)

(72) Inventors: James Na, San Diego, CA (US); David Imagawa, Oakland, CA (US); Fabio Tucci, San Diego, CA (US); Graham Beaton, San Diego, CA (US); Satheesh Ravula, San Diego, CA (US)

(73) Assignees: BRUIN BIOSCIENCES, INC., San Diego, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 309 days.

(21) Appl. No.: 16/616,808

(22) PCT Filed: May 25, 2018

(86) PCT No.: PCT/US2018/034744
§ 371 (c)(1),
(2) Date: Nov. 25, 2019

(87) PCT Pub. No.: WO2018/218208
PCT Pub. Date: Nov. 29, 2018

(65) Prior Publication Data
US 2021/0169801 A1 Jun. 10, 2021

Related U.S. Application Data

(60) Provisional application No. 62/511,898, filed on May 26, 2017, provisional application No. 62/511,895, filed on May 26, 2017.

(51) Int. Cl.
| | |
|---|---|
| *A61K 9/127* | (2006.01) |
| *A61P 35/00* | (2006.01) |
| *A61K 9/14* | (2006.01) |
| *A61K 9/50* | (2006.01) |
| *A61K 31/404* | (2006.01) |
| *A61K 31/44* | (2006.01) |
| *A61K 31/47* | (2006.01) |
| *A61K 31/53* | (2006.01) |
| *A61K 47/24* | (2006.01) |

(52) U.S. Cl.
CPC ............ *A61K 9/127* (2013.01); *A61K 9/1277* (2013.01); *A61K 9/146* (2013.01); *A61K 9/5026* (2013.01); *A61K 31/404* (2013.01); *A61K 31/44* (2013.01); *A61K 31/47* (2013.01); *A61K 31/53* (2013.01); *A61K 47/24* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 3,426,011 | A | 2/1969 | Parmerter et al. |
| 6,652,883 | B2 | 11/2003 | Goupil et al. |
| 6,676,971 | B2 | 1/2004 | Goupil et al. |
| 7,235,576 | B1 | 6/2007 | Riedl et al. |
| 7,351,834 | B1 | 4/2008 | Riedl et al. |
| 7,947,282 | B2 | 5/2011 | Noujaim et al. |
| 8,318,199 | B2 | 11/2012 | Kim et al. |
| 8,481,075 | B2 | 7/2013 | Xiaoping et al. |
| 8,697,137 | B2 | 4/2014 | Vogel et al. |
| 8,741,351 | B2 | 6/2014 | Vogel et al. |
| 8,877,953 | B2 | 11/2014 | Grunenberg et al. |
| 9,375,442 | B2 | 6/2016 | Zhang et al. |
| 9,724,421 | B2 | 8/2017 | Denys et al. |
| 9,737,488 | B2 | 8/2017 | Schuckler et al. |
| 9,827,196 | B2 * | 11/2017 | Mescheder ............. A61P 19/02 |
| 2003/0206864 | A1 | 11/2003 | Mangin |
| 2003/0208864 | A1 | 11/2003 | Kohler |
| 2003/0211165 | A1 | 11/2003 | Vogel et al. |
| 2004/0013728 | A1 * | 1/2004 | Oh ............................ B82Y 5/00 424/468 |
| 2007/0098724 | A1 | 5/2007 | Noujaim et al. |
| 2007/0281028 | A1 | 12/2007 | Lewis et al. |
| 2009/0092675 | A1 * | 4/2009 | Puri ...................... A61K 9/1635 424/501 |
| 2010/0209512 | A1 | 8/2010 | Driscoll et al. |
| 2011/0020427 | A1 * | 1/2011 | Zhang .................. A61K 31/407 514/459 |

(Continued)

FOREIGN PATENT DOCUMENTS

| | | |
|---|---|---|
| EP | 3150203 | 4/2017 |
| JP | 2013544278 | 12/2013 |

(Continued)

OTHER PUBLICATIONS

FDA (https://www.accessdata.fda.gov/drugsatfda_docs/label/2010/021923s008s009lbl.pdf) (Year: 2010).*
Bibi et al (J Microencapsulation, 2012, 29(3), 262-276) (Year: 2012).*
Eisai (https://www.eisai.com/news/pdf/enews201406pdf.pdf) (Year: 2014).*
Dass et al (Drug Delivery, 7:1, 15-19, 2000) (Year: 2000).*
International Search Report PCT/US2018/034744, Prepared by the U.S. Patent and Trademark Office, dated Aug. 24, 2018, 3 pages.
Feng Dai et al. Liposomal curcumin inhibits hypoxia-induced angiogenesis after transcatheter arterial embolization in VX2 rabbit liver tumors. Onco Targets Ther. Sep. 15, 2015; 8:2601-11.

(Continued)

*Primary Examiner* — Celeste A Roney
(74) *Attorney, Agent, or Firm* — Brooks Kushman PC; John E. Nemazi

(57) ABSTRACT

A chemoembolization therapy, which combines therapeutic effects of peripheral arterial occlusion with the local administration of an anti-cancer agent. A particle or microsphere occludes the arteries providing blood flow to the tumor, resulting in tumor oxygen deprivation. The anti-angiogenic agent is an anti-cancer drug.

12 Claims, 12 Drawing Sheets

(56) References Cited

U.S. PATENT DOCUMENTS

| | | | |
|---|---|---|---|
| 2012/0093932 | A1 | 4/2012 | Li et al. |
| 2012/0201867 | A1 | 8/2012 | Lewis et al. |
| 2012/0288441 | A1 | 11/2012 | O'Gara |
| 2013/0011467 | A1 | 1/2013 | Zhang et al. |
| 2013/0324548 | A1* | 12/2013 | Denys .................. A61P 9/00 514/252.18 |
| 2014/0274945 | A1 | 9/2014 | Blaskovich et al. |
| 2015/0079155 | A1 | 3/2015 | Jensen et al. |
| 2017/0056327 | A1 | 3/2017 | Mi et al. |

FOREIGN PATENT DOCUMENTS

| | | |
|---|---|---|
| JP | 2015520233 | 7/2015 |
| WO | WO2012073188 | 6/2012 |
| WO | WO2014092858 | 6/2014 |
| WO | WO2014184726 | 11/2014 |

OTHER PUBLICATIONS

Sebastien Strieth et al. Neovascular targeting chemotherapy: encapsulation of paclitaxel in cationic liposomes impairs functional tumor microvasculature. Int J Cancer. May 20, 2004;110(1):117-24.

R. Salem et al. Chemoembolization and Radioembolization for Hepatocellular Carcinoma. Clin. Gastroenterol. Hepatol. (2013) 11: 604-611.

Parvinian et al. Pharmacokinetic study of conventional sorafenib chemoembolization in a rabbit VX2 liver tumor model. Diagn. Interv. Radiol. 2015; 21:235-240.

K.Y Tam et al. Chemoembolization agents for cancer treatment. European Journal of Pharmaceutical Sciences vol. 44, Issues 1-2, Sep. 18, 2011, pp. 1-10.

A Laurent et al. Trisacryl gelatin microspheres for therapeutic embolization, I: development and in vitro evaluation. AJNR Am J Neuroradiol. Mar. 1996;17(3):533-40.

R Beaujeux et al. Trisacryl gelatin microspheres for therapeutic embolization, II: preliminary clinical evaluation in tumors and arteriovenous malformations AJNR Am J Neuroradiol. Mar. 1996;17(3):541-8.

Leida Zhang et al. Transarterial chemoembolization (TACE) plus sorafenib versus TACE for intermediate or advanced stage hepatocellular carcinoma: a meta-analysis. PLoS One. Jun. 19, 2014;9(6):e100305.

Andrew L Lewis et al. Pharmacokinetic and safety study of doxorubicin-eluting beads in a porcine model of hepatic arterial embolization. J Vasc Interv Radiol. Aug. 2006;17(8):1335-43.

Wolfgang Sieghart et al. Conventional transarterial chemoembolisation in combination with sorafenib for patients with hepatocellular carcinoma: a pilot study. Eur Radiol (2012) 22:1214 1223.

Masatoshi Kudo et l. Transarterial Chemoembolization in Combination with a Molecular Targeted Agent: Lessons Learned from Negative Trials (Post-TACE, Brisk-Ta, Space, Oriental, and TACE-2). Oncology 2017;93(suppl 1):127-134.

Altaf S. Darvesh et al. Curcumin and Liver Cancer: A Review. Current Pharmaceutical Biotechnology, 2012, 13, 218-228.

Zhoujing Cheng et al. The combination therapy of transarterial chemoembolisation and sorafenib is the preferred palliative treatment for advanced hepatocellular carcinoma patients: a metaanalysis. World Journal of Surgical Oncology (2020) 18:243.

Sapna Puppala. Technical update on transcatheter arterial chemoembolization. Hepatoma Res. 2019;5:44.

Amr S Abu Lila et al, Recent advances in tumor vasculature targeting using liposomal drug delivery systems, The University of Tokushima, Institute of Health Biosciences, Department of Pharmacokinetics and Biopharmaceutics, Expert Opin. Drug Deliv. (2009), pp. 1298-1308.

* cited by examiner

CHEMOEMBOLIZATION AGENTS

CROSS-REFERENCE TO RELATED APPLICATIONS

This application is the U.S. national phase of PCT Application No PCT/US2018/034744 filed on May 25, 2018, which claims the benefit of U.S. Provisional Patent Application No. 62/511,895 filed on May 26, 2017, and U.S. Provisional Patent Application No. 62/511,898 filed on May 26, 2017, the disclosures of which are incorporated in their entirety by reference herein.

BACKGROUND

Field of the Disclosure

This disclosure relates to the field of cancer treatment. Described herein are compounds, compositions, and formulations, for addressing cancer in a subject. Also described herein are methods of treating cancer, specifically liver cancer, using the compounds, compositions, and formulations described herein.

Vascularized solid tumors manifest in many organs. For example, liver cancer is an aggressive illness that occurs as hepatocellular carcinoma (HCC) or as a metastasis from other organs, such as the colon, ovaries or stomach. Untreated, the prognosis of patients with such cancers is poor. Surgical resection remains the gold standard for the treatment of both HCC and colorectal metastases. Destruction of liver tumors in situ is sometimes possible with the use of radiofrequency ablation, microwave ablation, cryoablation, nanoknife ablation, radioembolization, and systemic chemotherapy. Other vascularized solid tumors are found in kidney cancers or lung cancers.

In addition to the treatment methods above, chemoembolization is a treatment method that has been utilized for treating vascularized solid tumors such as HCC, as well as other solid tumors. This method involves two therapeutic purposes, the occlusion of vasculature supplying blood to the tumor via the embolization effect (tumor necrosis), and the delivery of an anti-cancer drug into the tumor via elution of the drug material attached to the embolization agent. The combination of embolization and drug delivery, or chemoembolization, has been found to be superior to the treatment of cancer as compared with embolization alone.

In chemoembolization methods, an embolizing particle or microsphere is loaded with an anti-cancer drug to provide a chemoembolization agent, which is then fed into the blood supply of the tumor. These embolizing particles or microspheres physically occlude the blood vessel or vessels which feed the tumor and reduce or halt the flow of blood to the tumor so as to induce necrosis. Additionally, separation of the anti-cancer drug from the embolizing particles or microspheres also occurs, and because such separation is localized to the tumor, a high concentration of the drug is achieved while minimizing the systemic concentration of the drug and its accompanying side effects.

SUMMARY

Disclosed herein are chemoembolization agents including weakly charged or uncharged and/or poorly water soluble agents attached to embolizing particles or microspheres for treatment of solid tumors. In some embodiments, the solid tumors are solid vascularized tumors. In some embodiments, the solid vascularized tumors are hepatic tumors. In some embodiments, the solid vascularized tumors do not include hepatic tumors.

In one aspect, a chemoembolization agent for treatment of vascularized solid tumors is provided. The chemoembolization agent includes an embolizing particle or microsphere, an encapsulating agent, the encapsulating agent affixed to or attached to the embolizing particle or microsphere through ionic or other non-covalent interactions, and the encapsulating agent being a liposome, and a therapeutic agent contained within the encapsulating agent, the therapeutic agent being uncharged or weakly charged or the therapeutic agent having low solubility in aqueous media at physiological pH, and the therapeutic agent being an anti-cancer agent being Sorafenib, Regorafenib, Lenvatinib, Tirapazamine, Cabozantinib, or Sunitinib. In some embodiments, the vascularized solid tumor is a liver cancer tumor or a kidney cancer tumor.

In some embodiments, the therapeutic agent is Sorafenib. In some embodiments, the therapeutic agent is Regorafenib. In some embodiments, the therapeutic agent is Lenvatinib. In some embodiments, the therapeutic agent is Tirapazamine. In some embodiments, the therapeutic agent is Sunitinib. In some embodiments, the therapeutic agent is Cabozantinib.

In another aspect, a chemoembolization agent is provided. The chemoembolization agent includes an embolizing particle or microsphere, an encapsulating agent, the encapsulating agent affixed to or attached to the embolizing particle or microsphere through ionic or other non-covalent interactions, and a therapeutic regimen contained within the encapsulating agent.

In some embodiments, the therapeutic agent is uncharged or weakly charged. In some embodiments, the therapeutic agent has low solubility in aqueous media at physiological pH. In some embodiments, the therapeutic regimen includes one or more therapeutic agents. In some embodiments, the one or more therapeutic agents is an anti-cancer agent. In some embodiments, the anti-cancer agent is positively charged. In some embodiments, the anti-cancer agent is negatively charged. In some embodiments, the anti-cancer agent is selected from Sorafenib, Regorafenib, Lenvatinib, Tirapazamine, Cabozantinib, or Sunitinib. In some embodiments, the anti-cancer agent is Sorafenib, Regorafenib, or Lenvatinib. In some embodiments, the encapsulating agent containing the encapsulated therapeutic agent releases or is configured to release the therapeutic agent. In some embodiments, the chemoembolization agent further includes a non-encapsulated therapeutic agent affixed to or attached to the embolizing particle or microsphere. In some embodiments, the non-encapsulated therapeutic agent is associated to the chemoembolization agent via a releasable mechanism. In some embodiments, the embolizing particle or microsphere is composed of a polyvinyl alcohol material. In some embodiments, the embolizing particle or microsphere includes one or more of DC Beads®, acetalized PVA (for example, Contour SE™, Boston Scientific, Natick, Mass., USA), cross-linked acrylic hydrogels (for example, Embospheres™, Biosphere, Rockland, Mass., USA), Embozene™ (Boston Scientific, Natick, Mass., USA), Oncozene™ (Boston Scientific, Natick, Mass., USA), LC Beads® (BTG), TheraSphere® (BTG), HepaSphere® and QuadraSphere® (Merit Medical), LifePearl® (Terumo), and HydroPearl® (Terumo). In some embodiments, the encapsulating agent is a liposome.

In some embodiments of the aspects above or the disclosure herein, the liposome is a cationic liposome. In some embodiments, the cationic liposome comprises a mixture of DOTAP and DOPC. In some embodiments, the relative amount of DOTAP and DOPC ranges from, and includes 10-90% DOTAP and 10-90% DOPC. In some embodiments, the relative amount of DOTAP and DOPC ranges from, and includes 20-80% DOTAP and 20-80% DOPC. In some embodiments, the relative amount of DOTAP and DOPC ranges from, and includes 30-70% DOTAP and 30-70% DOPC. In some embodiments, the relative amount of DOTAP and DOPC ranges from, and includes 40-60% DOTAP and 40-60% DOPC. In some embodiments, the cationic liposome comprises a mixture of about 50% DOTAP and 50% DOPC.

In another aspect, a pharmaceutical composition for the treatment of liver cancer is provided. The pharmaceutical composition includes a therapeutically effective amount of the chemoembolization agent of any of the aspects or embodiments herein disclosed.

In another aspect, a method of treating a cancer in a subject is disclosed. The method includes administering to a subject in need thereof a pharmaceutical composition as disclosed in any of the aspects or embodiments herein.

In some embodiments, the pharmaceutically effective amount of the chemoembolization agent is presented into a blood vessel that vascularizes a solid tumor of the cancer of a subject.

In some embodiments, the blood vessel is the hepatic artery. In some embodiments, the cancer is liver cancer. In some embodiments, the liver cancer is hepatocellular carcinoma. In some embodiments, the cancer is renal cell carcinoma. In some embodiments, the amount of therapeutic agent is administered to the subject at a dose of about 0.01 mg/kg of body weight to about 10 mg/kg body weight. In some embodiments, the amount of therapeutic agent is administered to the subject at a dose of about 0.1 mg/kg of body weight to about 2 mg/kg of body weight. In some embodiments, the amount of therapeutic agent is administered to the subject at a dose of about 0.5 mg/kg of body weight to about 1.5 mg/kg of body weight. In some embodiments, the amount of therapeutic agent is administered to the subject at a dose of about 1 mg/kg of body weight.

In another aspect, a method of preparing a chemoembolization agent is provided. The method includes the steps of encapsulating in a first aqueous media therapeutic agent within an encapsulating agent, the therapeutic agent being uncharged or weakly charged or being poorly water soluble, and contacting in a second aqueous media the encapsulating agent having the encapsulated therapeutic agent with a embolizing particle or microsphere so as to affix the encapsulating agent to the embolizing particle or microsphere.

In some embodiments, the therapeutic agent is an anticancer agent. In some embodiments, the encapsulating agent is a liposome.

In some aspects, methods of preparing the above chemoembolization agents are described. In some aspects, this disclosure describes methods of treating a subject with a cancer including a vascularized solid or semi-solid malignant tumor by presenting the chemoembolization agent to a blood vessel vascularizing the solid or semi-solid tumor.

The chemoembolization agents described and claimed herein have many attributes and embodiments, including, but not limited to, those set forth, or described, or referenced, in this Summary. The "Summary" section is not intended to be all-inclusive and the chemoembolization agents described and claimed herein are not limited to, or by the features or embodiments identified in, this "Summary" section, which is included for purposes of illustration only and not restriction. Additional embodiments are disclosed in the section entitled "Detailed Description of Certain Inventive Embodiments" below.

BRIEF DESCRIPTION OF THE DRAWINGS

Features of the present disclosure will become more fully apparent from the following description and appended claims, taken in conjunction with the accompanying drawings. It will be understood that these drawings depict only certain embodiments in accordance with the disclosure and, therefore, are not to be considered limiting of its scope; the disclosure will be described with additional specificity and detail through use of the accompanying drawings. An apparatus, system or method according to some of the described embodiments can have several aspects, no single one of which necessarily is solely responsible for the desirable attributes of the apparatus, system or method. After considering this discussion, and particularly after reading the section entitled "Detailed Description of Certain Inventive Embodiments" one will understand how illustrated features serve to explain certain principles of the present disclosure.

DETAILED DESCRIPTION OF CERTAIN INVENTIVE EMBODIMENTS

Figure 1:
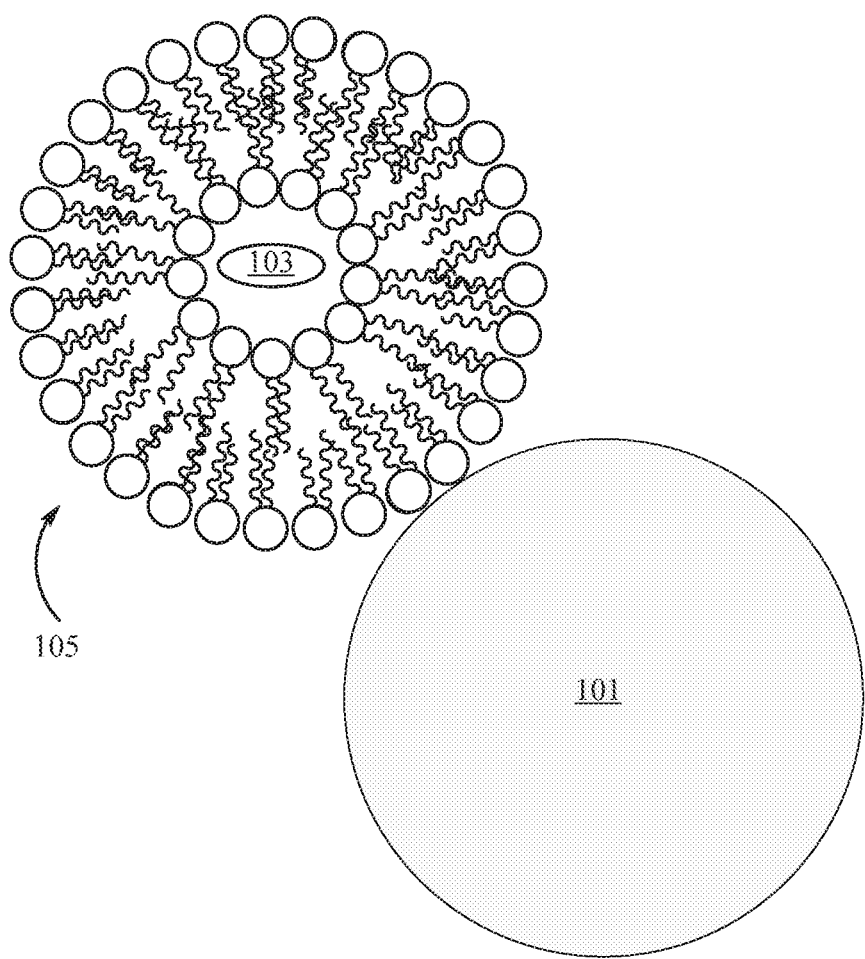
FIG. 1 depicts a liposome-encapsulated therapeutic agent associating with an embolizing particle or microsphere.

Described herein is a chemoembolization therapy, which combines therapeutic effects of peripheral arterial occlusion with the local administration of an anti-cancer agent. A particle or microsphere occludes the arteries providing blood flow to the tumor, resulting in tumor oxygen deprivation. The anti-cancer agent is an anti-cancer drug, as described herein.

1. Definitions

The term "cancer" refers to, or describes, the physiological condition in mammals that is typically characterized by unregulated cell growth and/or hyperproliferative activities. A "tumor" has one or a plurality cancerous cells. Examples of cancer include, but are not limited to, carcinoma, lymphoma, blastoma, sarcoma, and leukemia or lymphoid malignancies. More particular examples of such cancers include squamous cell cancer (for example, epithelial squamous cell cancer), lung cancer, including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulvar cancer, thyroid cancer, hepatic carcinoma, anal carcinoma, penile carcinoma, as well as head and neck cancer. In some embodiments, solid tumor cancers that may be treated by chemoembolization are sarcomas, carcinomas and lymphomas. Solid tumors including vascularized solid tumors can develop in any tissue or organ of the body, including lungs, breast, prostate, skin, liver and colon. In some embodiments, solid tumor cancers are malignant hypervascularized tumors, including hepatoma or hepatocellular carcinoma (primary liver cancer) and metastasis (spread) to the liver from: colon cancer, breast cancer, carcinoid tumors and other neuroendocrine tumors, islet cell tumors of the pancreas, ocular melanoma, sarcomas, and/or vascular primary tumors in the body.

The term "chemoembolization agent", as used herein, refers to a tripartite composition having (a) at least one therapeutic agent, (b) at least one encapsulating agent and (c) an embolizing particle or microsphere. In some embodiments, the embolizing particle or microsphere is oppositely charged with respect to the encapsulating agent(s) to allow for ionic interaction between the encapsulating agent(s) and embolizing particle or microsphere. In some embodiments, more than one encapsulating agent encapsulates at least one therapeutic agent. In some embodiments, the at least one therapeutic agent is an anti-cancer agent that is uncharged or weakly charged and/or has poor water solubility. In some embodiments, the at least one therapeutic agent is an anti-cancer agent that is charged and/or soluble in aqueous solution. In some embodiments, the at least one embolizing particle or microsphere and/or embolizing particle or microsphere interacts non-covalently with at least one non-encapsulated therapeutic agent. In some embodiments, the non-encapsulated therapeutic agent(s) are oppositely charged with respect to the encapsulating agent(s) or embolizing particle or microsphere. In some embodiments, the at least one encapsulated therapeutic agents and any other encapsulated therapeutic agents are releasable from the encapsulating agent(s). In some embodiments, the non-encapsulated therapeutic agent(s) are releasable from the embolizing particle or microsphere(s) and the embolizing particle or microsphere. Chemoembolization agents are further described by the embodiments disclosed herein.

The term "embolizing particle" or "embolizing microsphere" as used herein, refers to a particulate or microsphere material capable of swelling when contacted with a physiological fluid so as to increase in volume and in some embodiments, is a particle or microsphere that in a collection of such particles is capable of sufficient swelling for occluding, in whole or in part, a blood vessel to a vascularized tumor in a subject when delivered to the blood vessel. In some embodiments, an embolizing microsphere includes a polymer. In some embodiments, the embolizing microsphere is selected from sulfonate-modified polyvinyl alcohol hydrogel beads, carboxyl-modified polyvinyl alcohol-co-sodium acrylate beads, and sulfonate-modified N-Fil hydrogel, including without limitation microspheres of polyvinyl alcohol (PVA) (for example, DC Beads®, BTG), acetalized PVA (for example, Contour SE™, Boston Scientific, Natick, Mass., USA), cross-linked acrylic hydrogels (for example, Embospheres™, Biosphere, Rockland, Mass., USA), Embozene™ (Boston Scientific, Natick, Mass., USA), Oncozene™ (Boston Scientific, Natick, Mass., USA), LC Beads® (BTG), TheraSphere® (BTG), HepaSphere® and QuadraSphere® (Merit Medical), LifePearl® (Terumo), and HydroPearl® (Terumo). The microspheres typically range in diameter from approximately 50 microns to approximately 1000 microns, more typically in the range of approximately 100 microns to approximately 300 microns. Those and other embolizing microspheres are further described by the following embodiments.

"Encapsulating agent", as the term is used herein, refers to an organic moiety that encapsulates at least one therapeutic agent. The at least one therapeutic agents is an anti-cancer agent that is uncharged or weakly charged and/or has poor water solubility, and the organic moiety is capable of releasing the anti-cancer agent and any other therapeutic agents encapsulated therein or affixed non-covalently thereto. An encapsulating agent having a net positive charge is referred to as a cationic encapsulating agent and an encapsulating agent having a net negative charge is referred to as an anionic encapsulating agent, wherein the net charge is sufficient for maintaining ionic interactions with the embolizing particles or microspheres of opposite net charge during localized release of the encapsulated anti-cancer agent and any other therapeutic agents encapsulated therein or non-covalently affixed thereto to an extent sufficient to elicit desired therapeutic effect(s) from the released anti-cancer agent and any other released therapeutic agents(s). Encapsulating agents are further described by the following aspects and embodiments.

In some aspects the encapsulating agent is an anionic encapsulating agent and that agent is an anionic liposome or an anionic cyclodextrin. The anionic liposome or cyclodextrin when present in an aqueous solution at physiological pH has a net charge sufficient for ionic interaction with an oppositely charged embolizing particle of a chemoembolization agent such that the anionic encapsulating agent remains non-covalently associated with the embolizing particle or microsphere at least until the therapeutic agent(s)

contained within the encapsulating agent is(are) released to the physiological environment to which the chemoembolization agent is exposed. In some embodiments, the cyclodextrin is methylated cyclodextrin. In some embodiments, one or a plurality of the hydroxyl functional groups of the cyclodextrin is functionalized with a carboxylate, sulfonate, or phosphonate functional group. In some embodiments, the cyclodextrin is selected from: α (alpha)-cyclodextrin, β (beta)-cyclodextrin, γ (gamma)-cyclodextrin, 2-(hydroxypropyl)-beta-cyclodextrin, methyl 2-(hydroxypropyl)-beta-cyclodextrin extent of labeling 4-10 (determined by NMR (Sigma Aldrich, USA), (2-Hydroxypropyl)-γ-cyclodextrin, Methyl-β-cyclodextrin extent of labeling 1.5-2.1 methyl per 1 mol (Sigma Aldrich, USA), sulfobutylether-beta-cyclodextrin (SBE-beta-CD) or sulfobutylether-gamma-cyclodextrin (SBE-gamma-CD), the anionic cyclodextrins described in Sang et al., Bull. Korean Chem. Soc. 2013, Vol. 34, No. 7, pages 2016-2022, herein incorporated by reference in its entirety, the anionic cyclodextrins described in U.S. Pat. No. 3,426,011, herein incorporated by reference in its entirety. In some embodiments, the encapsulating agent is a component of a pharmaceutical composition including a therapeutically effective amount of the therapeutic agent.

In some embodiments, the encapsulating agent is a cationic encapsulating agent. In some embodiments, the cationic encapsulating agent includes a cationic liposome or a cationic cyclodextrin, and the cationic liposome or cyclodextrin when present in an aqueous solution at physiological pH having a net positive charge sufficient for ionic interaction with an anionic embolizing particle or microsphere of a chemoembolization agent such that the cationic encapsulating agent remains non-covalently associated with the anionic embolizing particle or microsphere. In some embodiments, the chemoembolization agent remains non-covalently associated with the anionic embolizing particle or microsphere at least until the therapeutic agent(s) contained within the encapsulating agent is released to the physiological environment to which the chemoembolization agent is exposed. In some embodiments, the cationic cyclodextrin is prepared by the reaction of any of the neutral cyclodextrins described herein with (2,3-epoxypropyl)trimethylammonium chloride, as described in Xiao, H., et al., J Colloid Interface Sci. 2005 Mar. 15; 283(2):406-13, herein incorporated by reference in its entirety. In some embodiments, the cationic cyclodextrin is prepared by the procedure described in Sang et al., Bull. Korean Chem. Soc. 2013, Vol. 34, No. 7, pages 2016-2022, herein incorporated by reference in its entirety.

The term "preventing" or "protecting" as used herein, means preventing in whole or in part, or ameliorating, or controlling.

The term "treating" as used herein, refers to both therapeutic treatment and prophylactic, or preventative measures, or administering an agent suspected of having therapeutic potential. The term includes preventative (for example, prophylactic) and palliative treatment.

The term "a pharmaceutically effective amount", as used herein, means an amount of active compound, or pharmaceutical agent, that elicits the biological, or medicinal, response in a tissue, system, animal, or human that is being sought, which includes alleviation or palliation of the symptoms of the disease being treated and/or an amount sufficient to have utility and provide desired therapeutic endpoint. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or a plurality of the symptoms associated with the cancer. To the extent the drug may prevent growth and/or kill existing cancer cells, it may be cytostatic and/or cytotoxic. For cancer therapy, efficacy can be measured, for example, by assessing the time to disease progression and/or determining the response rate.

The term "pharmaceutically acceptable", as used herein, means that the substance or composition must be compatible chemically and/or toxicologically, with the other ingredients including a formulation, and/or the mammal being treated therewith.

The term "releasable" as used herein, refers to the capability of an encapsulating agent of a chemoembolization agent to allow release of the encapsulated therapeutic agent(s) and diffusion of the released therapeutic agent(s) from the chemoembolization agent when the chemoembolization agent is exposed to serum under physiological conditions over suitable time period(s) for eliciting desired therapeutic effect(s) from the encapsulated therapeutic agent(s) released from the an encapsulating agent. In some embodiments, the at least one encapsulated therapeutic agent that is released is an anti-cancer agent, and the at least one anti-cancer agent is weakly charged and/or has poor water solubility, and further refers to the capability of a chemoembolization agent to allow diffusion away from the chemoembolization agent of the released encapsulated therapeutic agent(s) any other therapeutic agent(s) that were affixed non-covalently to the encapsulating agents and/or the embolizing particle.

The term "releasable mechanism" as used herein refers to a means by which one entity may be dissociated from another entity. In some embodiments, the releasable mechanism is the cleavage of a bond between a therapeutic agent and an embolizing particle or microsphere. In some embodiments, the bond cleavage is the hydrolysis of a hydrolytically unstable bond. The hydrolytically unstable bond can be an ester, a carbamate, an anhydride, an amide, and a silicon-oxygen-carbon bond. The cleavage can occur from a low or high pH, an esterase, or an amidase.

The terms "encapsulation", "encapsulating" and like terms as used herein, refers to the surrounding by an encapsulating agent of a therapeutic agent, the therapeutic agent being an anti-cancer agent that is uncharged or weakly charged and/or has poor water solubility. Without being bound by theory, the surrounding wholly or partially sequesters the anti-cancer agent any other therapeutic agent contained therein from the physiological environment to which a chemoembolization agent having that encapsulating agent is to be exposed, whereupon the exposure the sequestered anti-cancer and other sequestered therapeutic agents are released into that physiological environment.

The term "subject" as used herein, refers to an animal that is the object of treatment, observation or experiment. The term "subject" includes organisms which are capable of suffering from a cell proliferative disorder or a disorder associated with reduced or insufficient programmed cell death (apoptosis) or who could otherwise benefit from the administration of a compound, such as human and non-human animals. The term "cell proliferative disorder" includes disorders involving the undesired or uncontrolled proliferation of a cell and it includes disorders involving reduced or insufficient programmed cell death (apoptosis). In some embodiments, the cell proliferative disease is cancer. "Animal" includes mammals. "Mammal" includes, without limitation, mice; rats; rabbits; guinea pigs; dogs;

cats; sheep; goats; cows; horses; primates, such as monkeys, chimpanzees, apes, and prenatal, pediatric, and adult humans.

The term "therapeutic agent" as used herein, refers to a chemical compound that exerts a biological effect useful for the treatment of a disease or condition or alleviation of a symptom caused by the disease or condition or from an undesired side effect of a treatment of that disease or condition. Therapeutic agents include anti-cancer agents as described herein.

The term "anti-cancer agent" as used herein refers to a therapeutic agent that exerts a cytotoxic or cytostatic effect on hyper-proliferating cells when those cells or nearby cells are exposed to that agent. Anti-cancer agents include without limitation, tubulin disrupting agents, DNA damaging agents and protein kinase inhibitors. In some embodiments, the anti-cancer agent is selected from one or more of demethylation agents, retinoids, antimetabolites, antimicrotubule agents, anti-angiogenesis agents, alkylating agents, biological response modifiers, antitumor antibiotics, proteasome inhibitors, topoisomerase I inhibitors, topoisomerase II inhibitors, and phytochemicals including curcumin, theobromine, theophylline, anthocyanins (cyanidin, malvidin), carotenoids (Alpha-carotene, Beta-carotene, Beta-cryptoxanthine, luetin, Xeaxanthin, astaxanthin, lycopene), hydroxylcinnamic acids (Chicoric acid, coumarin, ferulic acid, scopoletin), flavones (apigenin, chrysin, luteolin, Daidzein, Genistein), flavonols (galalgin, fisetin), flavanones (eriodictyol, hespertin, naringenin), anthocyanidines (cyanidin, pelargonidin, delphinidin, peonidin, malvidin), isoflavonoids (genistein, daidzein, glycitein, formononetin), flavanoles (catechin, epicatechin, epigallocatechin, epicatechin gallate, epigallocatechin gallate), lignans (Silymarin), phenolic acids (capsaicin, ellagic acid, gallic acid, rosmarinic acid, tannic acid) organosulfides (allicin, glutathione, indole-3-carbinol, isothiocyanate sulforaphane), phytosterols (Beta-Sitosterol), stylbenes (Pterostilbene, Resveratrol), xanthophylls (Astaxanthin, Beta-Cryptoxanthin), tannins, saponins, steroids, phlobatannin, terpenoids (Geranlol, limenene), flavonoids (epicatechin, Hesperidin, Isohamnetin, Kaempferol, Myricetin, galangin, fisetin) Naringin, Nobiletin, Proanthocyanidins, Quercetin, Rutin, Tangeretin), hydroxyl benzoic acids (gallic acid, protocatechuic acid, vannilic acid, syringic acid), hydroxyl cinnamic acids (p-coumaric acid, caffeic acids, ferulic acid, sinapic acid), glycosides, hormones, immunomodulators, aromatase inhibitors, glucocorticosteroids, cytokines, enzymes, antiandrogen molecules, epigenetic modifiers, imatinib, Sorafenib, Regorafenib, Raf265, vemurafenib, dabrafenib, encorafenib, nilotinib, erlotinib, gefitinib, dasatinib, everolimus, cyclophosphamide, methotrexate, 5-fluorouracil, doxorubicin, cisplatin, carboplatin, oxaliplatin, nedaplatin, hydroxyurea, leucovorin calcium, tamoxifen, flutamide, asparaginase, altretamine, mitotane, procarbazine hydrochloride, mechlorethamine, thioguanine, carmustine, lomustine, temozolomide, melphalan, chlorambucil, streptozocin, methotrexate, vincristine, bleomycin, vinblastine, vindesine, dactinomycin, daunorubicin, lenalidomide, L-asparginase, tamoxifen or anti-proliferative agents such as rapamycin, paclitaxel or anti-angiogenesis agents such as avastin, or inhibitors of tyrosine kinase including epidermal growth factor receptor (EGFR), vascular endothelial growth factor receptor (VEGFR), platelet derived growth factor receptor (PDGFR), fibroblast growth factor receptor (FGFR), Rous sarcoma oncogene/Breakpoint cluster region/Abl (Src-bcr-abl), Insulin-like growth factor 1 receptor (IGF-1R), FLT-3, HER-2, STATS, c-Kit, c-Met, ALK, RAS, RAF, mutant B-RAF inhibitor, ETA receptor inhibitor, HIF inhibitor, Syk inhibitor, Tie2 kinase inhibitor and the like), Vascular disrupting agents (for example, plinabulin), cell cycle/check point inhibitors like polo-like kinase (PLK) inhibitor (for example, volasertib), cyclin dependent kinase (CDK) inhibitors (for example, seliciclib, indirubin etc.), topoisomerase inhibitors (for example, adriamycin, camptothecin, etoposide, idarubicin, irinotecan, topotecan, doxorubicin, mitoxantrone etc.), microtubule inhibitors for example, docetaxel, paclitaxel, vincristine etc.), antimetabolites (for example, decitabine, gemcitabine, fludarabine etc.) telomerase inhibitors, DNA & RNA replication inhibitors (for example, clarithromycin, cytarabine, mitoxantrone HCl, doxorubicin etc.,) dihydrofolate reductase inhibitor, HDAC inhibitor, Bcl-2 and TNF-α inhibitors, PARP inhibitors, MAPK inhibitors, PI3K/Akt/mTOR inhibitors, integrase and protease inhibitors, Wnt/Hedgehog/Notch inhibitors, cAMP, lipide signaling inhibitors (for example, PKC, PIM etc.), TGF-β inhibitors, chemotherapeutic pro-drugs, antioxidant inhibitors like diethyl-dithiocarbaate, methoxyestradiol, 1-buthionine sulfoximine, 3-amino-1,2,4-triazole, lapatinib, Sunitinib, meso-tetra(3-hydroxyphenyl)chlorine (m-THPC), hypericin, hormones, immunomodulators, aromatase inhibitors, glucocorticosteroids, cytokines, enzymes, anti-androgen molecules, epigenetic modifiers, nilotinib, lonafarnib, dasatinib, pazopanib, afatinib, alectinib, ceritinib, crizotinib, osimertinib, axitinib, Cabozantinib, brivanib alaniate, everolimus, and combinations thereof. In some embodiments, the anti-cancer agent is selected from Abiraterone Acetate, Abitrexate (Methotrexate), Abraxane (Paclitaxel Albumin-stabilized Nanoparticle Formulation), Adcetris (Brentuximab Vedotin), Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alkeran (Melphalan Hydrochloride), Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Atezolizumab, Avastin (Bevacizumab), Avelumab, Axitinib, Azacitidine, Becenum (Carmustine), Beleodaq, Belinostat, Bendamustine Hydrochloride, Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Brentuximab Vedotin, BuMel, Busulfan, Busulfex (Busulfan), Cabazitaxel, Cabometyx (Cabozantinib-S-Malate), Cabozantinib-S-Malate, Campath (Alemtuzumab), Camptosar (Irinotecan Hydrochloride), Capecitabine, Carboplatin, Carfilzomib, Carmubris (Carmustine), Carmustine, Casodex (Bicalutamide), Ceritinib, Cerubidine (Daunorubicin Hydrochloride), Cervarix, (Recombinant HPV Bivalent Vaccine), Cetuximab, Chlorambucil, Cisplatin, Clafen, Clofarabine, Clofarex, Clolar (Clofarabine), Cobimetinib, Cometriq (Cabozantinib-S-Malate), Cosmegen (Dactinomycin), Cotellic (Cobimetinib), Crizotinib, Cyfos (Ifosfamide), Cyramza (Ramucirumab), Cytarabine, Cytarabine Liposome, Cytosar-U (Cytarabine), Cytoxan, Dabrafenib, Dacarbazine, Dacogen (Decitabine), Dactinomycin, Daratumumab, Darzalex, Dasatinib, Daunorubicin Hydrochloride, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enzalutamide, Epirubicin Hydrochloride, Erbitux (Cetuximab), Eribulin Mesylate, Erivedge (Vismodegib), Erlotinib Hydrochloride, Erwinaze (Asparaginase Erwinia chrysanthemi), Etopophos (Etoposide Phosphate), Etoposide, Etoposide Phosphate, Evacet (Doxorubicin Hydrochloride Liposome), Everolimus, Evista (Raloxifene Hydrochloride), Evomela (Melphalan Hydrochloride), Exemestane, 5-FU (Fluorouracil), Fareston (Toremifene), Farydak (Panobinostat), Faslodex (Fulvestrant), Femara (Letrozole), Filgrastim, Fludara (Fludarabine Phosphate), Fludarabine Phosphate, Flutamide, Folex (Methotrexate), Folex PFS (Methotrexate), Folfiri, Folfiri-Bevacizumab, Folfiri-Cebuximab, Folfirinox, Folfox, Folotyn (Pralatrexate), Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine, Gemcitabine Hydrochloride, Gemcitabine-Cisplatin, Gemzar (Gemcitabine Hydrochloride), Gilotrif (Afatinib Dimaleate), Gleevec (Imatinib Mesylate), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Ibrance (Palbociclib), Ibritumomab Tiuxetan, Ibrutinib, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), IL-2 (Aldesleukin), Imatinib Mesylate, Imbruvica (Ibrutinib), Imiquimod, Imlygic (Talimogene Laherparepvec), Inlyta (Axitinib), Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Keytruda (Pembrolizumab), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex, Methazolastone (Temozolomide), Methotrexate, Methotrexate LPF, Mexate (Methotrexate), Mexate-AQ (Methotrexate), Mitomycin C, Mitoxantrone Hydrochloride, Mitozytrex (Mitomycin C), Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar, Netupitant and Palonosetron Hydrochloride, Neupogen (Filgrastim), Nexavar (Sorafenib Tosylate), Nilandron (Nilutamide), Nilotinib, Nilutamide, Ninlaro (Ixazomib Citrate), Nivolumab, Nolvadex (Tamoxifen Citrate), Nplate (Romiplostim), Obinutuzumab, Odomzo (Sonidegib), Ofatumumab, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), Osimertinib, Oxaliplatin, Paclitaxel, Paclitaxel Albumin-stabilized Nanoparticle Formulation, Palbociclib, Palifermin, Palonosetron Hydrochloride, Pamidronate Disodium, Panitumumab, Panobinostat, Paraplatin, Pazopanib Hydrochloride, Pegaspargase, Peginterferon Alfa-2b, PEG-Intron (Peginterferon Alfa-2b), Pembrolizumab, Pemetrexed Disodium, Perj eta (Pertuzumab), Pertuzumab, Platinol, Platinol-AQ, Plerixafor, Pomalidomide, Pomalyst, Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Revlimid (Lenalidomide), Rheumatrex (Methotrexate), Rituxan (Rituximab), Rituximab, Rolapitant Hydrochloride, Romidepsin, Romiplostim, Rubidomycin (Daunorubicin Hydrochloride), Ruxolitinib Phosphate, Sclerosol Intrapleural Aerosol (Siltuximab), Sipuleucel-T, Somatuline Depot (Lanreotide Acetate), Sonidegib, Sorafenib, Sorafenib Tosylate, Sprycel (Dasatinib), Steritalc, Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), Tabloid (Thioguanine), Tafinlar (Dabrafenib), Tagrisso (Osimertinib), Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq (Atezolizumab), Temodar (Temozolomide), Temozolomide, Temsirolimus, Thalidomide, Thalomid (Thalidomide), Thiotepa, Tirapazamine, Topotecan Hydrochloride, Toremifene, Torisel (Temsirolimus), Tositumomab and Iodine I 131 Tositumomab, Totect (Dexrazoxane Hydrochloride), Trabectedin, Trametinib, Trastuzumab, Treanda (Bendamustine Hydrochloride), Trifluridine and Tipiracil Hydrochloride, Tremelimumab, Trisenox (Arsenic Trioxide), Tykerb (Lapatinib Ditosylate), Unituxin (Dinutuximab), Uridine Triacetate, Vandetanib, Varubi (Rolapitant Hydrochloride), Vectibix (Panitumumab), Velban (Vinblastine Sulfate), Velcade (Bortezomib), Velsar (Vinblastine Sulfate), Vemurafenib, Venclexta (Venetoclax), Venetoclax, Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, Vismodegib, Vistogard (Uridine Triacetate), Voraxaze (Glucarpidase), Vorinostat, Votrient (Pazopanib Hydrochloride), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), Zytiga (Abiraterone Acetate), and combinations thereof.

"Physiologic pH" is the pH that normally prevails in the human body. It is approximately 7.4.

"Renal cell carcinoma" (RCC) is a kidney cancer that originates in the lining of the proximal convoluted tubule, a part of the very small tubes in the kidney that transport primary urine. RCC is the most common type of kidney cancer in adults, responsible for approximately 90-95% of cases.

The term "anti-cancer agent" also refers to the use of therapeutic biologics including but not limited to monoclonal antibodies, antibody fragments (including scFvs), and large molecular weight protein scaffolds and protein constructs. In some embodiment, therapeutic biologics or biological products include products such as vaccines, blood and blood components, allergenics, somatic cells, gene therapy, tissues, and recombinant therapeutic proteins. In some embodiments, therapeutic biologics includes oligonucleotides, siRNA, RNA or DNA aptamers, and combinations thereof. In some embodiments, the oligonucleotides, siRNA, or RNA or DNA aptamers can be from 8 base pairs to 300 base pairs in length. In some embodiments, therapeutic biologics includes RNA strands in the presence of Cas9 protein (CRISPR-associated protein-9 nuclease (Cas9) from Streptococcus pyogenes). In some embodiments, therapeutic biologics include sugars, proteins, or nucleic acids or combinations thereof. In some embodiments, therapeutic biologics includes cells and tissues. In some embodiments, therapeutic biologics are isolated from a variety of natural sources—human, animal, or microorganism.

The term "weakly charged" as used herein refers to the ionization state of a compound having heteroatoms that are not capable of being fully or partially ionized to form a positively or negative charged center within that compound when in contact with an aqueous medium buffered at pH 7 at ambient temperature and pressure or has weakly basic functional group(s) in which the pKa of the conjugate acid(s) of the group(s) is about 2 to about -2 or has weakly acidic functional group(s) having a pKa of about 8 to about 12. A compound having no functional group capable of at least partial ionization when in contact with an aqueous medium buffered at pH 7 at ambient temperature and pressure is considered uncharged. The charge of the compound will also be a function of the dielectric constant of the medium in which the compound is present. In some embodiments, the compound is in a medium selected from water, buffered solution, Ringer's solution, ethoxylated oils, olive oil, ethanol, dimethyl sulfoxide, or mixtures thereof.

The terms "water soluble", "water solubility", and like terms, as used herein, refers to the ability of a compound to act as a solute in an aqueous medium at physiological pH and ambient temperature and pressure and may do so through acquisition of at least a partially positively charged or negatively charged center on contact with the aqueous medium and/or through polar and/or hydrogen bonding interactions between solvent water molecules and hydrogen bond donor/acceptor functional groups of the compound solute. A compound is considered water soluble if in an aqueous medium at physiological pH and ambient temperature and pressure the mass part of solvent to mass part of compound required for dissolution ranges from 10:1 or less to about 30:1. A compound is sparingly soluble when that ratio ranges from about 30:1 to about 100:1, slightly soluble in the range from about 100:1 to about 1000:1, very slightly soluble in the range from about 1000:1 to about 10,000:1 and is practically insoluble beyond that range. A therapeutic compound that is sparingly soluble in water is considered to have poor water solubility. A compound or combination of compounds is considered to have low "solubility" or "poorly water soluble" if it is either sparingly soluble or very slightly soluble. Solubility can be defined with reference to water (aqueous) or be with reference to other possible solvents.

The term "liposome" as used herein, refers to a particle characterized by an amphipathic spherical or near spherical bilayer formed by van der Waals interactions between a plurality of hydrophobic moieties each capped by a polar head group and arranged in an alternating manner such that a polar head group of one hydrophobic moiety projects outwards to an external aqueous environment, while an adjacent hydrophobic moiety projects its polar head group inward. Liposomes can be classified according to their lamellarity (uni- and multi-lamellar vesicles), size (small, intermediate, or large) and charge (anionic, cationic and neutral) of the polar head groups. In some embodiments, a liposome particle contains other hydrophobic components each of which is intercalated between two hydrophobic moieties of the liposome particle such that the optional hydrophobic components are embedded within the bilayer so as to affect the fluidity of the bilayer. In some embodiments, liposomes encapsulate a weakly charged or uncharged and/or poorly water soluble therapeutic agent by encapsulating that agent within its interior so as to separate that therapeutic agent from the external aqueous environment. Liposome particles typically have a diameter ranging from about 0.025 um to about 2.5 um in which the hydrophobic moieties are linear or lightly branched saturated hydrocarbons. In some aspects, a liposome particle includes saturated phospholipids having acyl chains whose lengths are selected based upon the desired diameter of the liposome particle. In some embodiments, the phospholipid is selected from: Soybean phosphatidylcholine (SPC), Hydrogenated soybean phosphatidylcholine (HSPC), Egg sphingomyelin (ESM), Egg phosphatidylcholine (EPC), Dimyristoyl phosphatidylcholine (DMPC), Dipalmitoyl phosphatidylcholine (DPPC), Dioleoyl phosphatidylcholine (DOPC), Distearoyl phosphatidylcholine (DSPC), Dimyristoyl phosphatidylglycerol (DMPG), Dipalmitoyl phosphatidylglycerol (DPPG), Dioleoyl phosphatidylglycerol (DOPG), Distearoyl phosphatidylglycerol (DSPG), Dimyristoyl phosphatidylethanolamine (DMPE), Dipalmitoyl phosphatidylethanolamine (DPPE), Dioleoyl phosphatidylethanolamine (DOPE), Dimyristoyl phosphatidylserine (DMPS), Dipalmitoyl phosphatidylserine (DPP S), Dioleoyl phosphatidylserine (DOPS), 1,2-dioleoyl-3-trimethylammonium-propane (DOTAP), 1,2-dilauroyl-sn-glycero-3-phosphocholine (DLPC), 1,2-dimyristoyl-sn-glycero-3-phosphocholine (DMPC), 1,2-dimyristoyl-sn-glycero-3-phosphate (sodium salt) (DMPA.Na), 1,2-dipalmitoyl-sn-glycero-3-phosphate (sodium salt) (DPPA.Na), 1,2-dioleoyl-sn-glycero-3-phosphate (sodium salt) (DOPA.Na), 1,2-dimyristoyl-sn-glycero-3-phospho-(1'-rac-glycerol) (sodium salt) (DMPG.Na), 1,2-dipalmitoyl-sn-glycero-3-phospho-(1'-rac-glycerol) (sodium salt) (DPPG.Na), 1,2-dioleoyl-sn-glycero-3-phospho-(1'-rac-glycerol) (sodium salt) (DOPG.Na), 1,2-dimyristoyl-sn-glycero-3-phospho-L-serine (sodium salt) (DMPS.Na), 1,2-dipalmitoyl-sn-glycero-3-phospho-L-serine (sodium salt) (DPPS.Na), 1,2-dioleoyl-sn-glycero-3-phospho-L-serine (sodium salt) (DOPS.Na), 1,2-dioleoyl-sn-glycero-3-phosphoethanolamine-N-(glutaryl) (sodium salt) (DOPE-Glutaryl (Na)$_2$), 1',3'-bis[1,2-dimyristoyl-sn-glycero-3-phospho]-sn-glycerol (ammonium salt) (Tetramyristoyl Cardiolipin (Na)$_2$), 1,2-distearoyl-sn-glycero-3-phosphoethanolamine-N-[methoxy(polyethylene glycol)-2000] (ammonium salt) (DSPE-mPEG-2000, Na), 1,2-distearoyl-sn-glycero-3-phosphoethanolamine-N-[methoxy(polyethylene glycol)-5000] (ammonium salt) (DSPE-mPEG-5000.Na), 1,2-distearoyl-sn-glycero-3-phosphoethanolamine-N-[maleimide(polyethylene glycol)-2000] (ammonium salt) (DSPE-Maleimide PEG-2000, Na), 1,2-dioleoyl-3-trimethylammonium-propane (chloride salt) (DOTAP, Cl), 1,2-dihexanoyl-sn-glycero-3-phosphocholine (DHPC), and mixtures thereof, and salts thereof.

The term "non-covalent" interaction refers to ionic bonds, van der Waals interactions, hydrogen bonding, pi-pi stacking, dipole-dipole interactions, dipole-quadrupole interactions, quadrupole-quadrupole interactions, multipole-multipole interactions, or combinations thereof. Ionic interaction (or ionic bonding) is a type of chemical bonding that involves the electrostatic attraction between oppositely charged ions, and is the primary interaction occurring in ionic compounds. The ions are atoms that have gained one or more electrons (known as anions, which are negatively charged) and atoms that have lost one or more electrons (known as cations, which are positively charged). This transfer of electrons is known as electrovalence in contrast to covalence. In the simplest case, the cation is a metal atom and the anion is a nonmetal atom, but these ions can be of a more complex nature. In simpler words, an ionic bond is the transfer of electrons from a metal to a non-metal in order to obtain a full valence shell for both atoms.

The term "package insert" as used herein, refers to instructions customarily included in commercial packages of therapeutic products that contain information about the indications, usage, dosage, administration, contraindications and/or warnings concerning the use of such therapeutic products.

A "subject in need" of treatment is an animal, preferably a human, who has a tumor, a solid tumor or a cancerous solid tumor.

The term "therapeutic regimen" can include a "therapeutic agent" or one or more "therapeutic agents". A "therapeutic agent" is a compound which may have particular efficacy in treating disease according to the present disclosure if administered in a pharmaceutically effective amount, potentially as a "pharmaceutical composition".

The term "vascularize" or "vascularized" means provided (a tissue or structure) with blood vessels or made vascular.

2. Description and Embodiments

Disclosed herein is a chemoembolization agent that includes three elements: (a) an embolizing particle or microsphere, (b) an encapsulating agent and (c) a therapeutic regimen consisting of one or more suitable therapeutic agents, the therapeutic agent being either uncharged or weakly charged and/or having poor water solubility. The embolizing particle or microsphere may be any composition of matter in which a collection of such particles or microspheres is capable of occluding blood vessels or capillaries, which can occur by swelling of a plurality of the particles or microspheres of the collection when exposed to blood within the vessels or capillaries.

In some embodiments, the embolizing particle or microsphere is made from the material polyvinyl alcohol (PVA). An exemplary PVA microsphere is the DC Bead® manufactured by Biocompatibles UK Ltd. DC beads® present negatively charged sulfonate groups, which bind to positively charged encapsulating agents, which encapsulate at least one therapeutic agent. In some embodiments, the therapeutic agent is an uncharged or weakly charged anti-cancer agent. In some embodiments, the negatively charged sulfonate groups on the DC beads® bind to both positively charged encapsulating agents (which encapsulates at least one therapeutic agent) and to a positively charged therapeutic agent not encapsulated by the encapsulating agent.

Another exemplary embolizing particle or microsphere includes a sodium acrylate alcohol copolymer. In some embodiments, the sodium acrylate alcohol copolymer is Hepasphere™ microspheres, manufactured by Merit Medical (Utah, USA), which are sodium acrylate alcohol copolymer particles formed from the copolymerization of vinyl acetate and methyl acrylate. Hepaspheres are negatively charged and are capable of binding positively charged therapeutic compositions. Hepaspheres can expand up to four times their dry size when wetted. In some embodiments, the embolizing particle or microsphere is non-spherical functionalized polyvinyl alcohol beads, including Bearing nsPVA Embolization Particles™, manufactured by Merit Medical (Utah, USA).

In some embodiments, the embolizing particle or microsphere is sodium alginate microspheres, as described in US Pat. Publication No. US 20120093932, herein incorporated by reference in its entirety.

In some embodiments, the embolizing particle is a hydrogel microsphere coated with an inorganic perfluorinated polymer (Polyzene-F), known as Oncozene™ (Boston Scientific, Natick, Mass., USA).

In some embodiments, the mean average bead diameter (as measured by light scattering, for example, the Wyatt Dawn Heleos II) is from 50 to 1000 microns. In some embodiments, the mean average bead diameter is from 70-150 microns, 100-300 microns, 300-500 microns, or 500-700 microns, or any range between the aforementioned values.

Chemoembolization agents of the present disclosure may be useful, for example, in treatment of liver cancers. Liver tissues receive oxygen and nutrients through the portal vein and the hepatic artery, the latter of which comes out directly from the main artery. Normal liver tissues receive blood mainly from the portal vein, while tumor tissues receive blood mainly from the hepatic artery. Therefore, when an anti-cancer drug is selectively delivered to the hepatic artery in the form of a chemoembolization agent the tumor is selectively starved of nutrients while exposing it to the anti-cancer drug without having to block the portal vein. The net effect increases the effectiveness of the anti-cancer drug while minimizing harm to normal liver tissues.

In transcatheter arterial chemoembolization (TACE), a catheter is inserted into the femoral artery in the groin and is directed to the hepatic artery. After reaching the hepatic artery, a vascular contrast medium is injected to obtain information regarding the position, size, and vascularization of the hepatic tumor for deciding upon an appropriate chemoembolization treatment protocol. A thin tube with a thickness of about 1 mm is then inserted into the catheter for delivery of an anti-cancer drug in the form of the chemoembolization agent.

Clinical chemoembolization protocols include the use of doxorubicin- or irinotecan-coated particle or microspheres as the chemoembolization agent. These two anti-cancer drugs are positively charged under physiological conditions due to their basic amine component, and by combining these positively charged drugs with a negatively charged embolizing particle or microsphere, a drug coated embolization article is created for use in chemoembolization procedures. Unfortunately, both irinotecan and doxorubicin have not been shown in clinical studies to be efficacious in treating HCC.

Some important therapeutic agents, including many other anti-cancer agents, contain only weakly basic or weakly acidic functional groups or are uncharged under physiological conditions and/or are poorly water soluble, thus cannot be readily loaded onto embolizing particles or microspheres having a complementary charge. These therapeutic agents are poorly water soluble due to their lack of an acidic or basic functional group and/or solubilizing functionalities, and this presents a great challenge in the art of preparing chemoembolization agents that depend upon non-covalent associations with the embolizing particles or microspheres in an aqueous environment.

Sorafenib is a therapeutic agent given to patients in advanced stage of HCC ineligible for TACE. Sorafenib has been shown to extend overall survival; however, this drug is poorly tolerated with serious side effects from systemic administration. The addition of Sorafenib after TACE has been attempted in at least 5 randomized controlled trials to no avail. In humans, embolization with agents such as Sorafenib has not been performed because they cannot be loaded on commercially available embolic materials. Indeed, currently commercially available drug eluting embolics (DEE) require a charge and water solubility for drug loading. Therefore, agents used in TACE are limited to drugs that can be loaded on the beads rather than agents that are actually efficacious against HCC.

To address this, methods disclosed herein have been developed of loading weakly charged or uncharged, and/or poorly water soluble therapeutic agents onto embolizing particles or microspheres to create novel chemoembolization agents for the treatment of solid vascularized tumors, which can include or exclude hepatic tumors. Also disclosed herein are methods of loading charged and/or aqueous soluble therapeutic agents onto embolizing particles or microspheres, separately or in combination with weakly charged or uncharged, and/or poorly water soluble therapeutic agents loaded onto embolizing particles or microspheres, for the treatment of solid vascularized tumors, which can include or exclude hepatic tumors.

Disclosed herein are novel chemoembolization agents, including embolizing particles or microspheres as carriers for therapeutic agents that have not previously been utilized in chemoembolization, but which show suitable efficacy against certain types of solid vascularized tumors when administered as free drugs. The methods of the present disclosure are compatible with any anti-cancer agent. In some aspects, the at least one therapeutic agent is an anti-cancer agent that is an uncharged or weakly charged and/or insoluble or poorly soluble in water, or otherwise bind poorly to embolizing particles. In some aspects, the anti-cancer agent is charged and/or soluble in aqueous solution. In some aspects, anti-cancer agent is encapsulated by a positive or negatively charged encapsulating agent to form a partially or fully loaded encapsulating agent resulting from the encapsulation is non-covalent affixed to oppositely charged embolizing particles or microspheres to provide a chemoembolization agent.

In some aspects, the partially or fully loaded encapsulating agent forms a non-covalent interaction with embolizing particles or microspheres to provide a chemoembolization agent.

In some aspects, the chemoembolization agent includes an embolizing particle or microsphere. In some aspects, the chemoembolization agent includes an encapsulating agent. In some aspects, the chemoembolization agent includes a therapeutic regimen, which includes one or more encapsulated therapeutic agents which are an uncharged or weakly charged and/or poorly water soluble anti-cancer agent, or a therapeutic agent which is charged and/or soluble in aqueous solution, or combinations thereof; and an encapsulating agent. In some aspects, the non-covalent interaction between the partially or fully loaded encapsulating agent and the embolizing particle or microsphere results from an ionic interaction between a charged partially or fully loaded encapsulating agent and an oppositely charged embolizing particle or microsphere. In some aspects, the embolizing particle or microsphere is affixed to the encapsulated therapeutic agent through non-covalent ionic interactions. In some aspects, the non-covalent interaction between the partially or fully loaded encapsulating agent and the embolizing particle or microsphere results from hydrogen bonding between the partially or fully loaded encapsulating agent and the embolizing particle or microsphere. In some aspects, the chemoembolization agent further includes a non-encapsulated therapeutic agent. In some aspects, the non-encapsulated therapeutic agent is affixed to the embolizing particle or microsphere and/or the encapsulating particle or microsphere through non-covalent interactions. In some aspects, the non-encapsulated therapeutic agent is affixed to the embolizing particle or microsphere agent and/or the encapsulating particles or microsphere through a non-covalent interaction selected from: ionic bonds, van der Waals interactions, hydrogen bonding, pi-pi stacking, dipole-dipole interactions, dipole-quadrupole interactions, quadrupole-quadrupole interactions, multipole-multipole interactions, or combinations thereof. In some aspects, the embolizing particle or microsphere interacts with more than one type of encapsulating agent. In some aspects, the more than one type of encapsulating agent is selected from a liposome or a cyclodextrin. In some aspects, each of the more than one type of encapsulating agent encapsulates different types of therapeutic agents. In some aspects, the embolizing particle or microsphere includes one or more encapsulating agents and interacts with a non-encapsulated therapeutic agent which may be a different type of therapeutic agent than those in the encapsulating agents. In some aspects, an embolizing particle or microsphere encapsulates an anti-cancer agent. In some aspects, the anti-cancer agent is uncharged or weakly charged and/or has low solubility in an aqueous media at physiological pH. In some aspects, the anti-cancer agent is charged and/or has high solubility in an aqueous media at physiological pH. In some aspects, the encapsulated therapeutic agent contains at least one encapsulated anti-cancer agent that can release the anti-cancer agent and any other encapsulated therapeutic agents and any encapsulating agents from the chemoembolization agent.

2.1 Therapeutic Agent

The compositions of the disclosure and the related methods of making them are applicable to any therapeutic agent, including small molecule drugs, biologics, peptides, antibodies, antibody fragments (for example, single chain variable fragments, or scFvs) and other drug classes. This disclosure describes methods which are particularly useful as applied to uncharged, weakly charged, and/or poorly water soluble anti-cancer agents, which do not readily associate with embolizing particles or microspheres.

Without being bound by theory, the encapsulating agent increases the solubility of the therapeutic agent in solution compared to the therapeutic agent in water alone, while simultaneously forming an ionic association complex with the embolization particle or microsphere.

Figure 10:
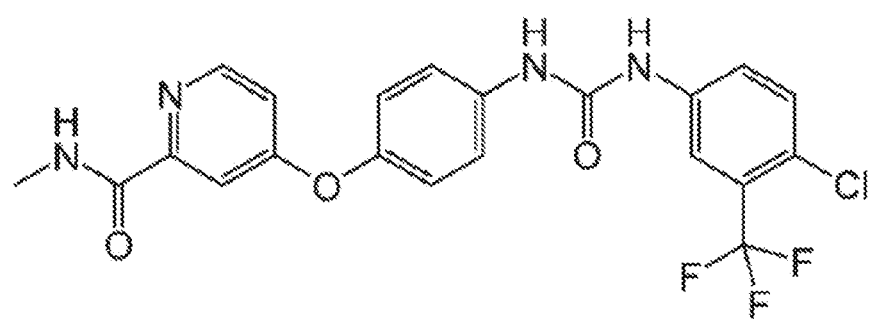
FIG. 10 is a drawing of the chemical structure of Sorafenib.

In some embodiments, the therapeutic agent is an anti-cancer agent. In some embodiments, the anti-cancer agent is Sorafenib, which is marketed as Nexavar™ by Bayer Healthcare (USA) for the treatment of HCC and is currently the only approved cancer drug for the treatment of HCC. Sorafenib is a biaryl urea, with the IUPAC chemical name of 4-{4-[3-(4-chloro-3-trifluoro-phenyl)-ureido]-phenoxyl}-pyridine-2-carboxylic methylamine. The molecular weight of Sorafenib is 464.8 g/mol. Clinical uses of Sorafenib can include its tosylate salt. The molecular formula of Sorafenib tosylate is $C_{21}H_{16}C_1F_3N_4O_3 \cdot C_7H_8O_3S$, the formula weight is 637.0 g/mol. The water solubility of Sorafenib is very poor but increases slightly under acid conditions. Sorafenib is slightly soluble in alcohol but is fully soluble in polyethylene glycol 400. Without being bound by theory, Sorafenib exhibits at least two modes of anti-tumor activity. Sorafenib is a Raf kinase inhibitor. Sorafenib inhibits the RAS/RAF/MEK/ERK signal transduction pathway by inhibiting the activity of RAF so as to inhibit tumor cell growth directly. Sorafenib also interrupts neovascularization of tumor thereby starving the nutrient and oxygen supply of tumor cells by inhibiting the activity of several tyrosine kinase receptors involved in neovascularization and the development of tumors, including vascular endothelial growth factor receptor 2 (VEGFR-2), REGFR-3, platelet derived growth factor receptor β (PDGFR-β) and proto-oncogene C-kit, resulting in an indirect inhibition of tumor cell growth. Sorafenib, systemically applied, has been shown to be effective against various types of solid tumors including HCC, renal cell carcinoma, thyroid cancer, brain, lung, and desmoid tumors. The chemical structure of Sorafenib is depicted in FIG. 10.

Figure 11:
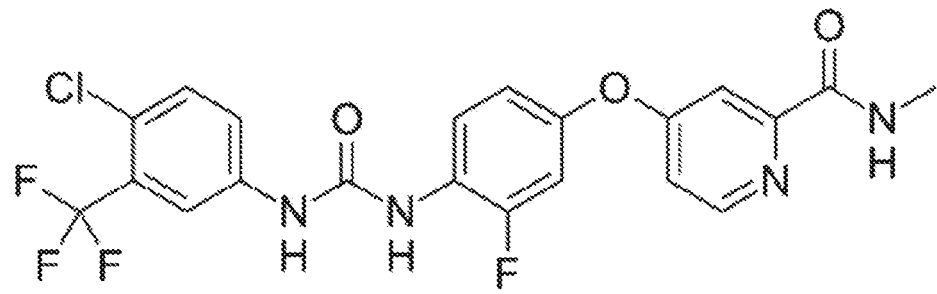
FIG. 11 is a drawing of the chemical structure of Regorafenib.

In some embodiments, the anti-cancer agent is Regorafenib. Regorafenib is marketed as Stivarga™ by Bayer Healthcare (USA). The structure of Regorafenib is similar to Sorafenib, having an additional fluorine atom located on the central ring of the molecule. Like Sorafenib, the water solubility of Regorafenib is poor, but increases in acidic conditions. Regorafenib is an inhibitor of multiple receptor tyrosine kinases. When applied systemically, Regorafenib has been found to be effective against various types of tumors, including metastatic colorectal cancers and gastrointestinal stromal tumors, the two indications for which it is FDA approved. The chemical structure of Regorafenib is depicted in FIG. 11.

Figure 12:
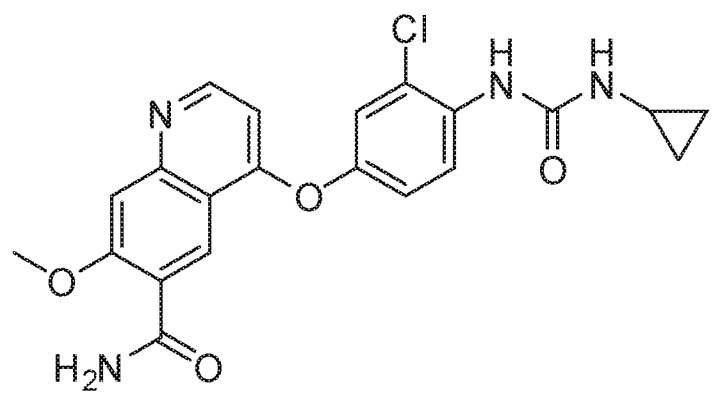
FIG. 12 is a drawing of the chemical structure of Lenvatinib.
Figure 13:
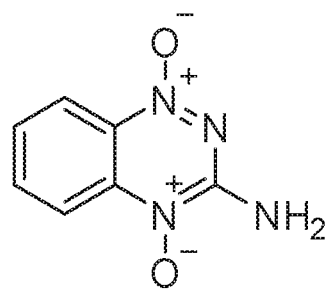
FIG. 13 is a drawing of the chemical structure of Tirapazamine.
Figure 14:
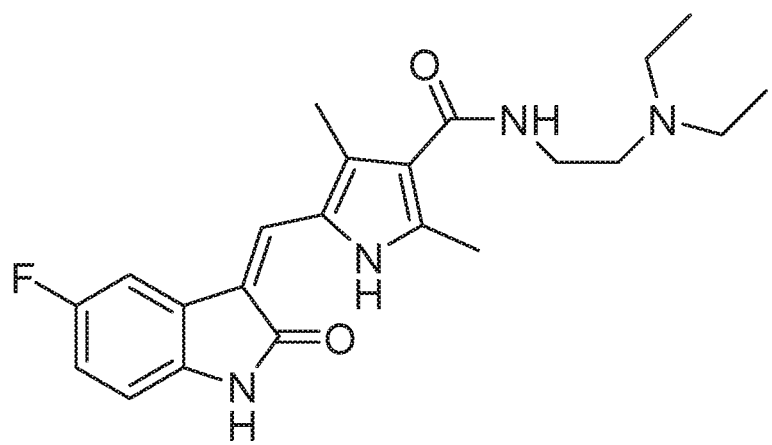
FIG. 14 is a drawing of the chemical structure of Sunitinib.

In some embodiments, the anti-cancer agent is Lenvatinib. The chemical structure of Lenvatinib is depicted in FIG. 12. In some embodiments, the anti-cancer agent is Tirapazamine. The chemical structure of Tirapazamine is depicted in FIG. 13. In some embodiments, the anti-cancer agent is Sunitinib. The chemical structure of Sunitinib is depicted in FIG. 14.

In some embodiments, where more than one anti-cancer agent is employed in the preparation of a chemoembolization agent, at least one of the anti-cancer agents is both charged and water soluble. In some embodiments, the anti-cancer agent is Doxorubicin (Adriamycin™). In some embodiments, the anti-cancer agent is Sunitinib (Sutent™).

2.2 Loading of Therapeutic Compounds into Chemoembolizing Agent

In some embodiments, in a first step, the therapeutic agent(s) is(are) encapsulated in a water soluble, charged encapsulating agent. In some embodiments, at least one of the therapeutic agents is an uncharged or weakly charged and/or poorly water soluble anti-cancer agent. In some embodiments, the therapeutic agent and the selected lipids are dissolved in dehydrated ethanol and this solution is added dropwise to a 10% trehalose solution under stirring. The resulting viscous emulsion is stirred at room temperature for 5 minutes and then filtered through a manual liposomal extruder using a 200 nm polycarbonate membrane. The resulting unilamellar liposomal solution is lyophilized overnight to yield a white solid. The solid is treated with deionized water yielding a final therapeutic agent at a concentration of 5 mg/mL. The liquid solution is decanted and DC Beads® (2 mL) are treated with the liposomal solution. The concentration of therapeutic agent in the supernatant is measured over time by HPLC/MS.

In some embodiments, the encapsulating agent is a liposome particle. The uncharged or weakly charged and/or poorly water soluble anti-cancer agent along with any additional therapeutic agents to be encapsulated are dissolved or suspended in an aqueous media solution containing lipids capable of forming liposomes. Next, liposome particles are formed from the solution using sonication or extrusion.

In some embodiments, when the uncharged or weakly charged and/or poorly water soluble anti-cancer agent is to be affixed to a negatively charged embolizing particle or microsphere, cationic lipids are used to form the liposome, which will act as the cationic encapsulating agent. In some embodiments, when the anti-cancer agent is to be affixed to a positively charged embolizing particle, anionic lipids are used to form the liposome, which will act as the anionic encapsulating agent. In some embodiments, the positively charged embolizing particle is a cationic polymer particle. In some embodiments, the cationic polymer particle includes glycidyl-trimethylammonium chloride (GTMAC) with polyvinyl alcohol (for example, Fetehi, et al., European Polymer Journal, 47, (2011), Pages 997-1004).

In some embodiments, the liposomes are cationic liposomes. The cationic liposomes can include or exclude DOTAP and DOPC. In some embodiments, the liposomes includes a mixture of DOTAP (1,2-dioleoyl-3-trimethylammonium-propane chloride salt) and DOPC (1,2-dioleoyl-sn-glycero-3-phosphocholine). The molar ratio of DOTAP to DOPC can be about 1:9, 2:8, 3:7, 4:6, 5:5, 6:4, 7:3, 8:2, or 9:1. In some embodiments, the liposome mixture may include 30-70% DOTAP and 30-70% DOPC. In some embodiments, the DOTAP and DOPC are present in a ratio of approximately 1:1. In some embodiments, the liposome composition may include stabilizing agents including for example but not limited to cholesterol (Al Asmari A K, Ullah Z, Tariq M, Fatani A. Preparation, characterization, and in vivo evaluation of intranasally administered liposomal formulation of donepezil. Drug Des Devel Ther 2016 10 p. 205-15 and Kieler-Ferguson H M, Chan D, Sockolosky J, Finney L, Maxey E, Vogt S, Szoka F C Jr4. Encapsulation, controlled release, and antitumor efficacy of cisplatin delivered in liposomes composed of sterol-modified phospholipids. Eur J Pharm Sci 2017 103 p. 85-93, which are both incorporated herein by reference).

In some embodiments, the liposomes are anionic liposomes. The anionic liposomes can be selected from free fatty acids and lysophospholipids. In some embodiments, the anionic liposomes can include or exclude: cholesteryl hemisuccinate (CHEMS), 1-stearoyl-2-hydroxy-sn-glycero-3-phosphate (sodium salt) (LPA), dioctanoylglycerol pyrophosphate (ammonium salt) (DGPP), 5-(palmitoyloxy)octadecanoic acid (5-PAHSA), 9-(palmitoyloxy)octadecanoic acid (9-PAHSA), 2-hydroxyoleic acid (sodium salt) (2-OHOA), α-mycolic acid, N-oleoylglycine, N-arachidonoylglycine, and N-palmitoylglycine.

In another embodiment, a cyclodextrin is utilized as the encapsulating agent. Cyclodextrins have been used as "carrier molecules" to encapsulate poorly water soluble compounds and impart aqueous solubility to these compounds. The cavity of cyclodextrins is hydrophobic and can accommodate lipid-soluble molecules, whereas the outer rims can be chemically modified to incorporate water soluble groups. The size of the cavity determines what types of compounds can be encapsulated. The cavity diameter of β-cyclodextrins has been found to be the most appropriate size for hormones, vitamins, and other drug-like compounds frequently used in drug discovery. Therefore, in some embodiments β-cyclodextrin and chemically modified β-cyclodextrin analogues that possess a cationic group on its wider rim are used to encapsulate an uncharged or weakly charged and/poorly water solubility negatively charged drug eluting beads.

2.3 Association of the Encapsulating Agent to Embolizing Particles

In the second step, the encapsulating agent containing the encapsulated therapeutic agent is affixed non-covalently to the embolizing particle or microsphere. In some embodiments, the therapeutic agent is uncharged or weakly charged and/or poorly water soluble. In some embodiments, the affixing step is accomplished by incubating the drug-containing liposomes particle or other drug-containing encapsulating agent with the embolizing particles or microsphere for sufficient time to saturate the surface of the embolizing particles with the liposomes or other encapsulating agents. In some embodiments, the incubation time is about 1 hour, about 2 hours, about 3 hours, about 4 hours, about 5 hours, about 6 hours, about 7 hours, about 8 hours, about 9 hours, about 10 hours, about 20 hours, about 30 hours, about 40 hours, about 50 hours, about 60 hours, about 70 hours, about 80 hours, about 90 hours, about 100 hours, or any time between the aforementioned times. The encapsulating agent will be adsorbed onto or reversibly bound to the embolizing particle or microspheres. The incubation can be done in the presence or absence of external agitation. The incubation can be done at normal or enhanced gravitational conditions. The enhanced gravitational conditions can be done by centrifuging the reaction solution during agitation. In some embodiments, the incubation is done at room temperature without agitation. In some embodiments, the incubation is done at a temperature between 0° C. to 80° C. In some embodiments, the incubation is done at 15° C. to 25° C.

FIG. 1 illustrates an embodiment where a therapeutic agent 103 is encapsulated in liposome 105 associated with embolizing particle or microsphere 101.

Figure 2:
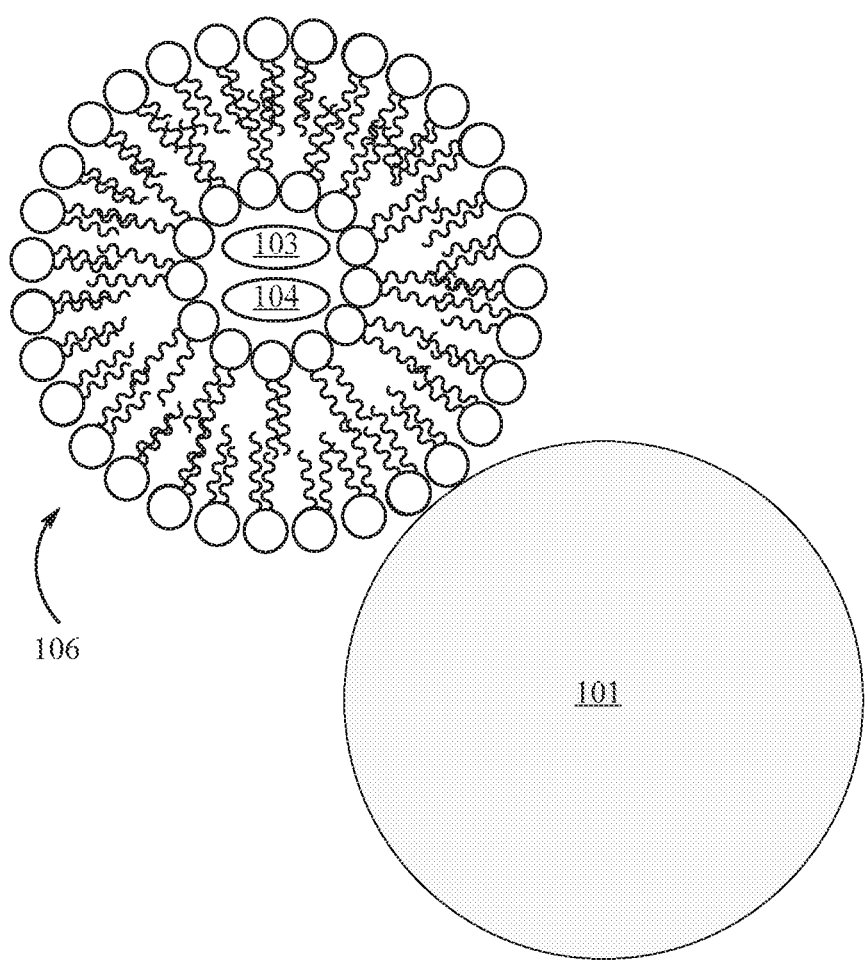
FIG. 2 depicts a liposome encapsulating two different therapeutic agents and the association of the liposome with an embolizing particle or microsphere.

FIG. 2 illustrates an embodiment where therapeutic agent 103 and another type of therapeutic agent 104 are both encapsulated in liposome 106 including both the therapeutic agent 103 and the therapeutic agent 104. Liposome 106 is associated with embolizing particle or microsphere 101.

Figure 3:
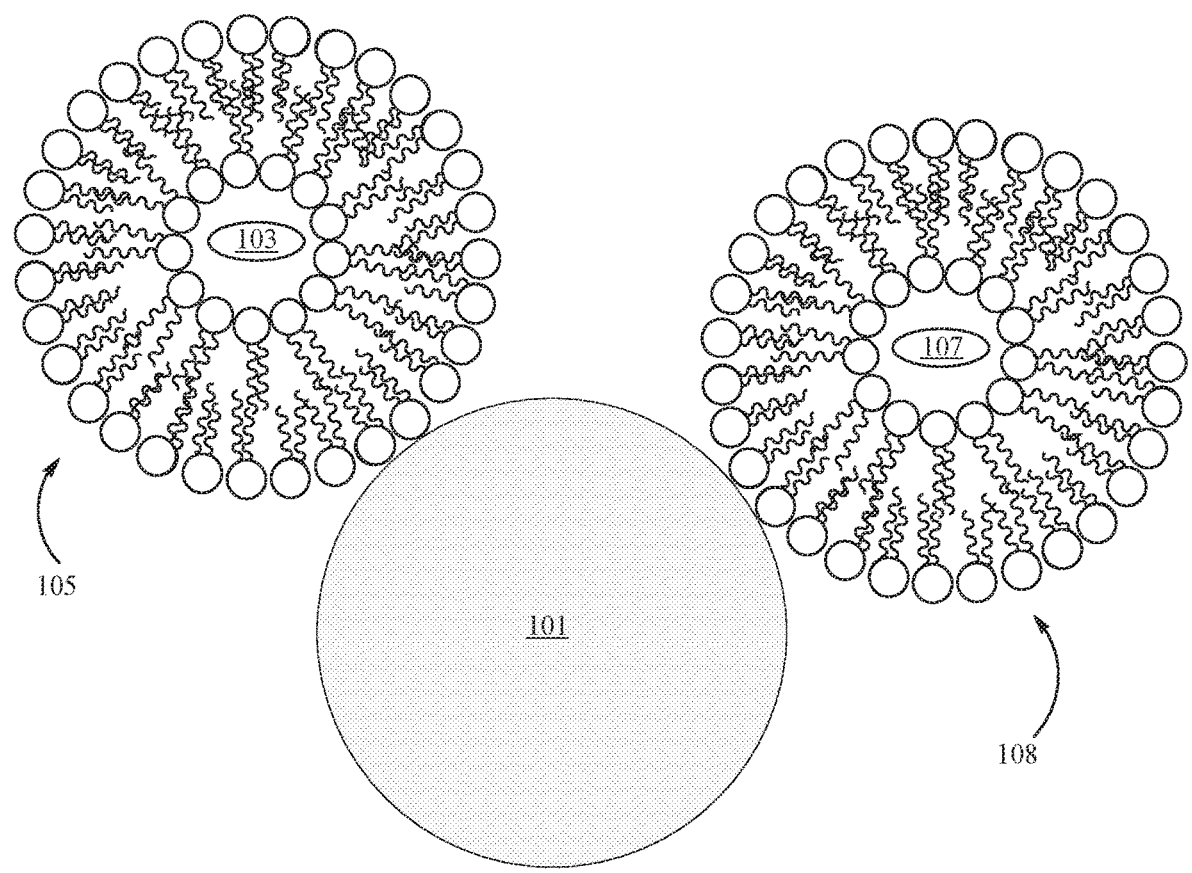
FIG. 3 depicts liposomes separately encapsulating two different therapeutic agents and the association of the liposomes with an embolizing particle or microsphere.

FIG. 3 illustrates an embodiment where therapeutic agent 103 is encapsulated in liposome 105 and another type of therapeutic agent 107 is encapsulated in another type of liposome 108, and both liposomes 105, 108 are associated with embolizing particle or microsphere 101. In some embodiments, therapeutic agent 103 is Sorafenib, Regorafenib or Lenvatinib, or combinations thereof, and the other type of therapeutic agent 107 is Sunitinib or doxorubicin or other anti-cancer agents that are charged, aqueous soluble, or both.

Figure 4:
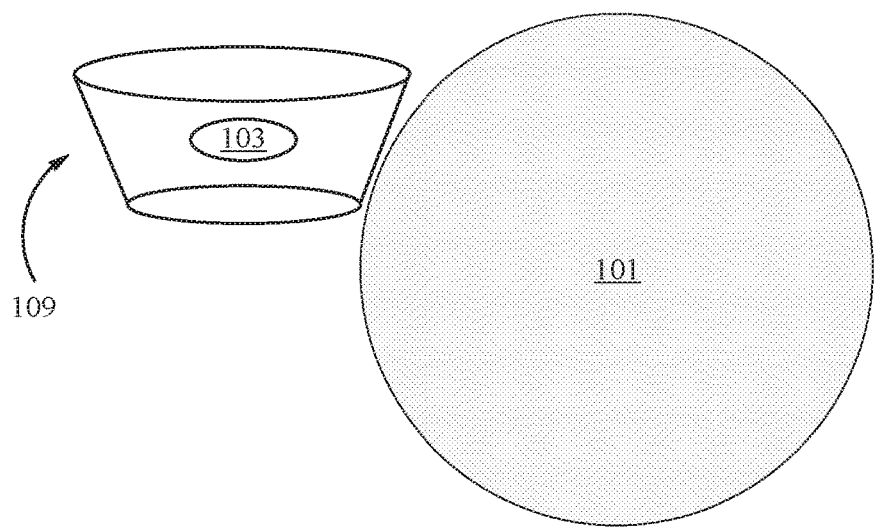
FIG. 4 depicts a cyclodextrin-encapsulated therapeutic agent associating with an embolizing particle or microsphere.

FIG. 4 illustrates an embodiment where therapeutic agent 103 is encapsulated in cyclodextrin 109, which is associated with embolizing particle or microsphere 101.

Figure 5:
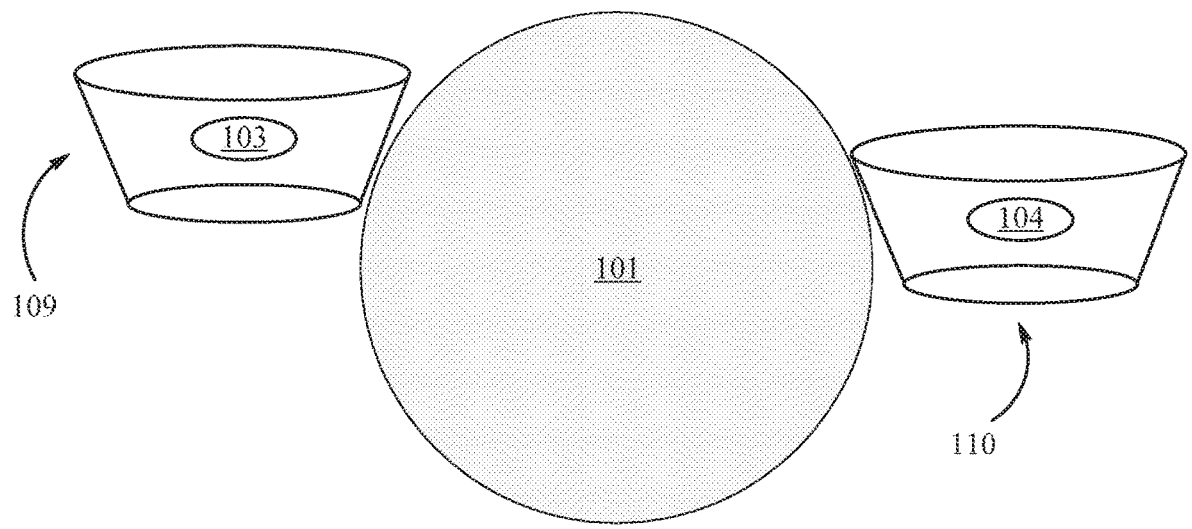
FIG. 5 depicts cyclodextrin molecules separately encapsulating two different therapeutic agents and the association of the cyclodextrin molecules with an embolizing particle or microsphere.

FIG. 5 illustrates an embodiment where therapeutic agent 103 is encapsulated in cyclodextrin 109 and another type of therapeutic agent 104 is encapsulated in another type of cyclodextrin 110, and both are associated with embolizing particle or microsphere 101.

Figure 6:
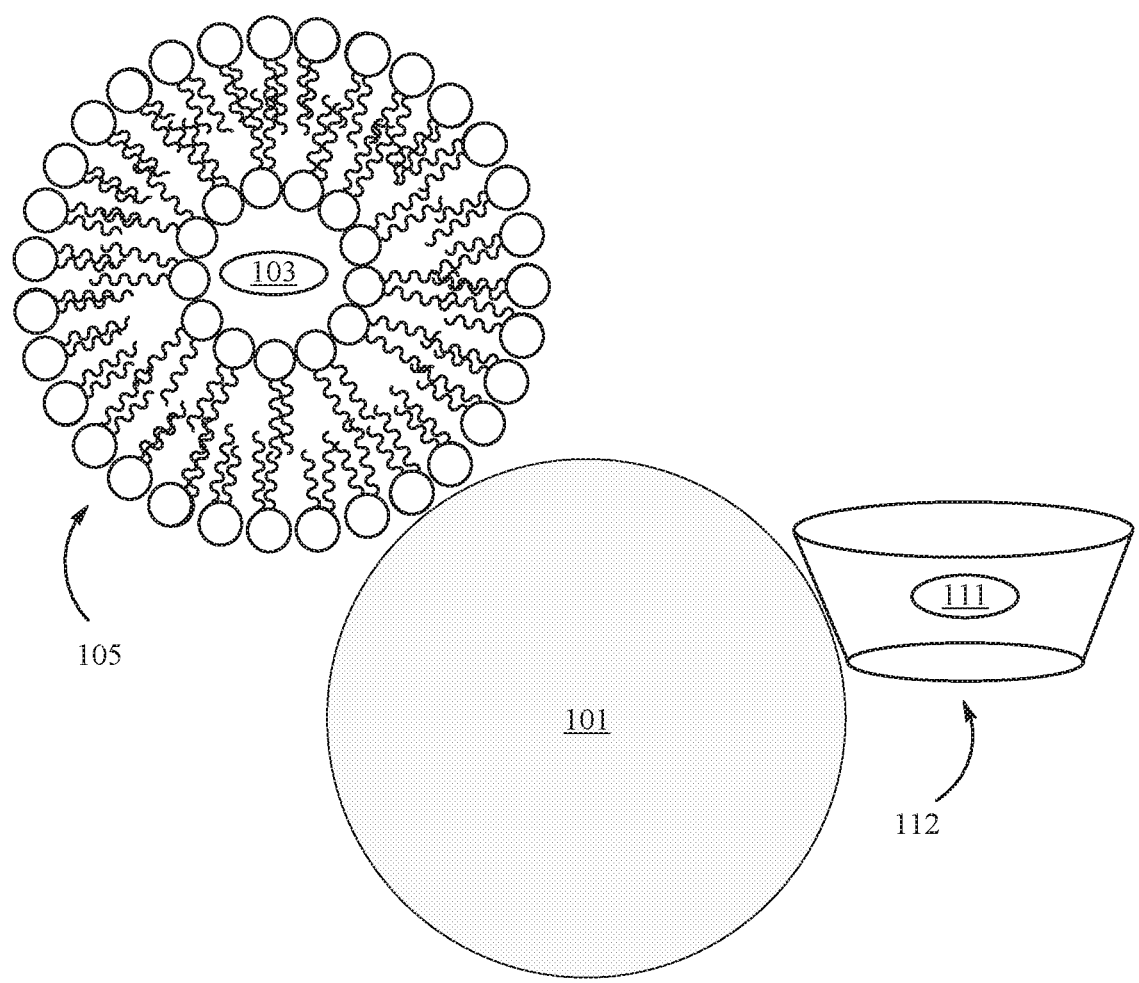
FIG. 6 depicts both a liposome-encapsulated therapeutic agent and a cyclodextrin-encapsulated therapeutic agent associating with an embolizing particle or microsphere.

FIG. 6 illustrates an embodiment where therapeutic agent 103 is encapsulated in liposome 105 and another type of therapeutic agent 111 is encapsulated in cyclodextrin 112, and both the liposome 105 and the cyclodextrin 112 are associated with embolizing particle or microsphere 101.

Figure 7:
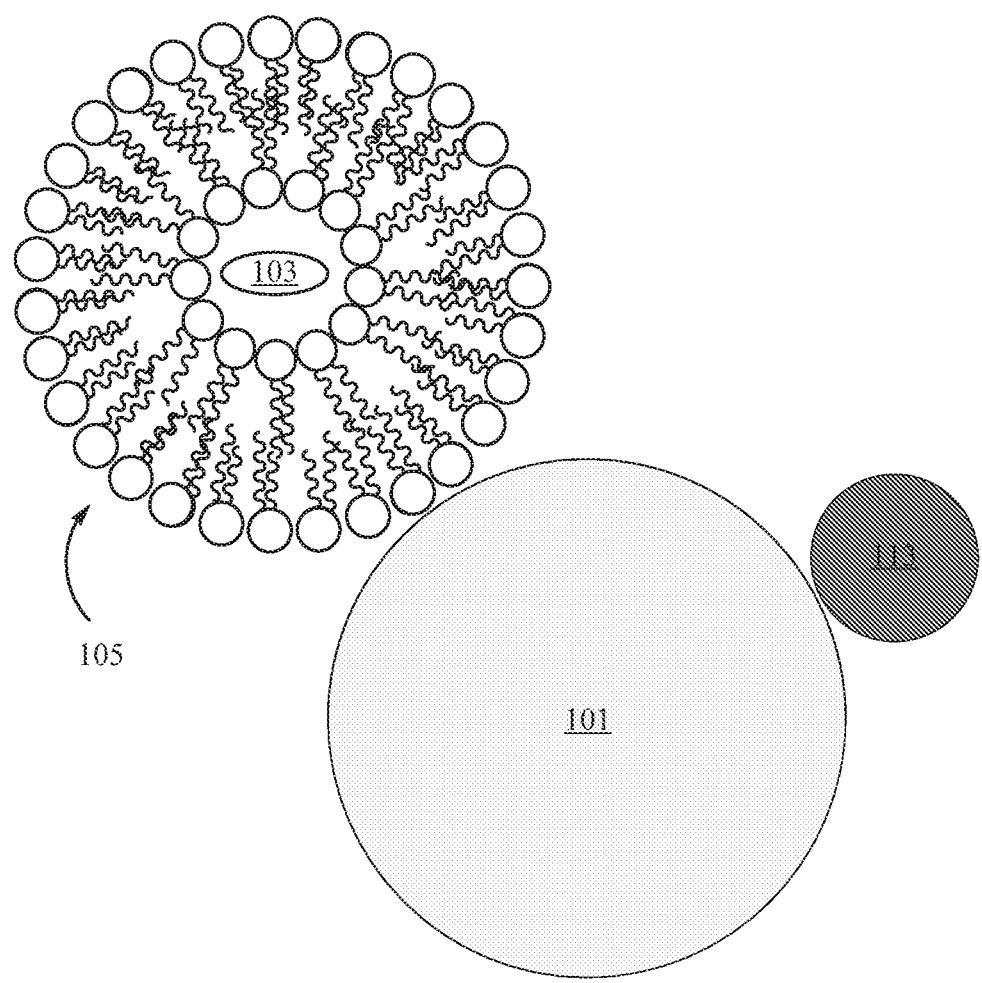
FIG. 7 depicts both a liposome-encapsulated therapeutic agent and a non-encapsulated therapeutic agent associating with an embolizing particle or microsphere.

FIG. 7 illustrates an embodiment where therapeutic agent 103 is encapsulated in liposome 105 and therapeutic agent 113 is not encapsulated and both the liposome 105 and the non-encapsulated therapeutic agent 113 are associated with embolizing particle or microsphere 101. In some embodiments, the therapeutic agent 103 is Sorafenib, Regorafenib, Lenvatinib, or combinations thereof, and therapeutic agent 113 is doxorubicin or Sunitinib or another anti-cancer agent that is charged, is aqueous soluble, or combinations thereof.

Figure 8:
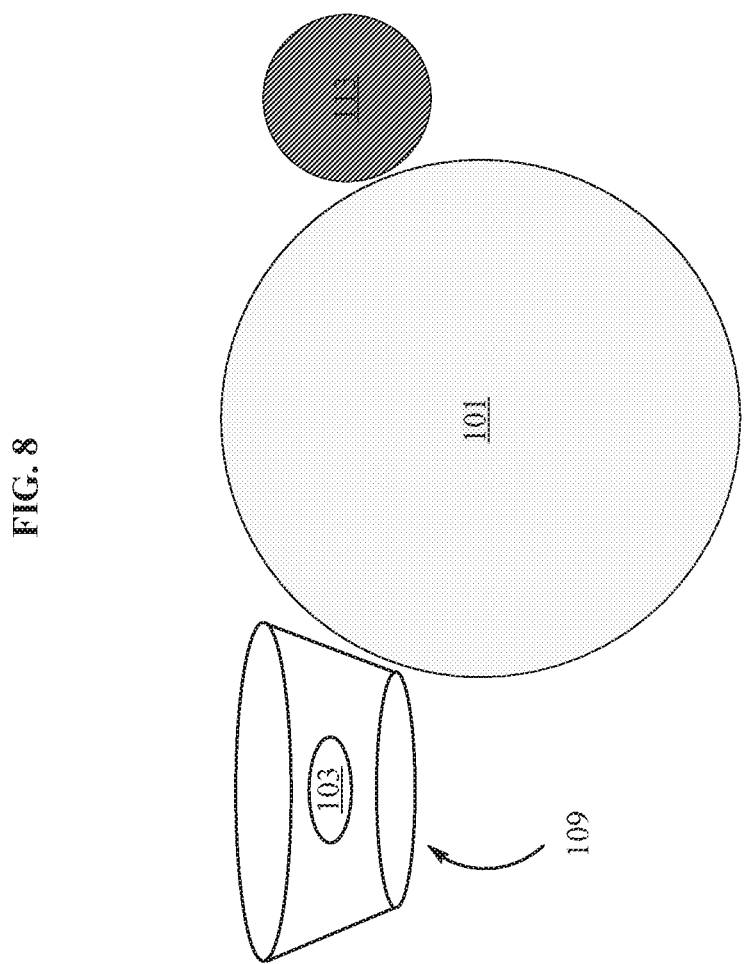
FIG. 8 depicts both a liposome-encapsulated therapeutic agent and a non-encapsulated agent associating with an embolizing particle or microsphere.

FIG. 8 illustrates an embodiment where therapeutic agents 103 is encapsulated in cyclodextrin 109 and therapeutics agent 113 is not encapsulated and both the cyclodextrin 109 and the non-encapsulated therapeutic agent 113 are associated with embolizing particle or microsphere 101.

Figure 9:
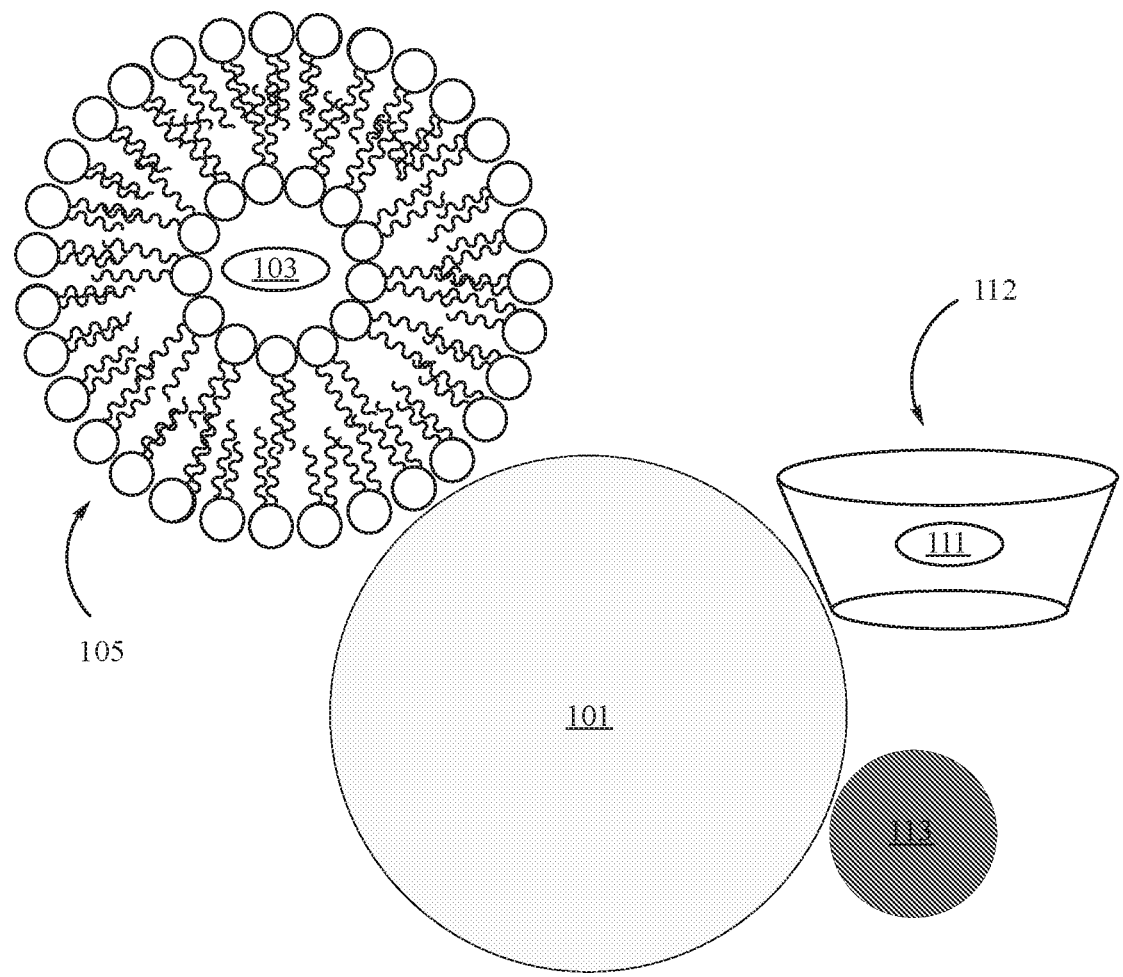
FIG. 9 depicts a liposome-encapsulated therapeutic agent, a cyclodextrin-encapsulated agent, and a non-encapsulated agent all associating with an embolizing particle or microsphere.

FIG. 9 illustrates an embodiment where therapeutic agent 103 is encapsulated in liposome 105 and another type of therapeutic agent 111 is encapsulated in cyclodextrin 112 and yet another type of therapeutic agent 113 is not encapsulated and the liposome 105, the cyclodextrin 112, and the non-encapsulated therapeutic agent 113 are all associated with embolizing particle or microsphere 101.

Preferred embodiments for the chemoembolization agent include compositions in which the embolizing particles or microspheres are selected from DC Beads®, acetalized PVA, cross-linked acrylic hydrogels, Embozene™, Oncozene™, LC Beads®, TheraSphere®, HepaSphere®, QuadraSphere®, LifePearl®, and HydroPearl®, the encapsulating agents are selected from DOTAP and DOPC and the therapeutic regimen comprises one or more therapeutic agents. The therapeutic agents in some embodiments included and may be selected from Sorafenib, Regorafenib, Lenvatinib, Tirapazamine, Cabozantinib, doxorubicin and Sunitinib. Other embodiments may include one or more other therapeutic agents disclosed herein.

Still other preferred embodiments for the chemoembolization agent include compositions in which the embolizing particles or microspheres are selected from DC Beads®, Oncozene™, the encapsulating agents are selected from DOTAP and DOPC and the therapeutic regimen comprises one or more therapeutic agents selected from Sorafenib, Regorafenib, Lenvatinib, Tirapazamine, Cabozantinib, doxorubicin or Sunitinib.

In a preferred embodiment, the embolizing particles or microspheres are DC Beads®, the encapsulating agents are DOTAP and DOPC and the therapeutic regimen comprises Sorafenib (Nexavar™).

In another preferred embodiment, the embolizing particles or microspheres are DC Beads®, the encapsulating agents are DOTAP and DOPC and the therapeutic regimen comprises Regorafenib (Stivarga™).

In another preferred embodiment, the embolizing particles or microspheres are DC Beads®, the encapsulating agents are DOTAP and DOPC and the therapeutic regimen comprises Tirapazamine.

In another preferred embodiment, the embolizing particles or microspheres are DC Beads®, the encapsulating agents are DOTAP and DOPC and the therapeutic regimen comprises Lenvatinib.

In a preferred embodiment, the embolizing particles or microspheres are DC Beads®, the encapsulating agents are DOTAP and DOPC and the therapeutic regimen comprises Sorafenib (Nexavar™) and Tirapazamine.

In another preferred embodiment, the embolizing particles or microspheres are DC Beads®, the encapsulating agents are DOTAP and DOPC and the therapeutic regimen comprises Regorafenib (Stivarga™) and Tirapazamine.

In another preferred embodiment, the embolizing particles or microspheres are DC Beads®, the encapsulating agents are DOTAP and DOPC and the therapeutic regimen comprises Lenvatinib and Tirapazamine.

In a preferred embodiment, the embolizing particles or microspheres are Oncozene™, the encapsulating agents are DOTAP and DOPC and the therapeutic regimen comprises Sorafenib (Nexavar™).

In another preferred embodiment, the embolizing particles or microspheres are Oncozene™, the encapsulating agents are DOTAP and DOPC and the therapeutic regimen comprises Regorafenib (Stivarga™).

In another preferred embodiment, the embolizing particles or microspheres are Oncozene™, the encapsulating agents are DOTAP and DOPC and the therapeutic regimen comprises Tirapazamine.

In another preferred embodiment, the embolizing particles or microspheres are Oncozene™, the encapsulating agents are DOTAP and DOPC and the therapeutic regimen comprises Lenvatinib.

In another preferred embodiment, the embolizing particles or microspheres are Oncozene™, the encapsulating agents are DOTAP and DOPC and the therapeutic regimen comprises Sorafenib (Nexavar™) and Tirapazamine.

In another preferred embodiment, the embolizing particles or microspheres are Oncozene™, the encapsulating agents are DOTAP and DOPC and the therapeutic regimen comprises Regorafenib (Stivarga™) and Tirapazamine.

In another preferred embodiment, the embolizing particles or microspheres are Oncozene™, the encapsulating agents are DOTAP and DOPC and the therapeutic regimen comprises Lenvatinib and Tirapazamine.

In still other preferred embodiments, the chemoembolization agent is prepared from a mixture of embolizing particles, an encapsulating agent(s), an encapsulated therapeutic agent and embolizing particles to which are non-covalently attached therapeutic agents which are charged and/or water soluble (as depicted in FIG. 7). In one preferred embodiment, the embolizing particles or microspheres are DC Beads®, the encapsulating agents are DOTAP and DOPC and the therapeutic regimen comprises encapsulated Sorafenib (Nexavar™) and Doxorubicin (Adriamycin™).

In one preferred embodiment, the embolizing particles or microspheres are DC Beads®, the encapsulating agents are DOTAP and DOPC and the therapeutic regimen comprises encapsulated Sorafenib (Nexavar™) and Sunitinib (Sutent™).

In another preferred embodiment, the embolizing particles or microspheres are DC Beads®, the encapsulating agents are DOTAP and DOPC and the therapeutic regimen comprises encapsulated Regorafenib (Stivarga™) and Doxorubicin (Adriamycin™).

In another preferred embodiment, the embolizing particles or microspheres are DC Beads®, the encapsulating agents are DOTAP and DOPC and the therapeutic regimen comprises encapsulated Regorafenib (Stivarga™) and Sunitinib (Sutent™).

In another preferred embodiment, the embolizing particles or microspheres are DC Beads®, the encapsulating agents are DOTAP and DOPC and the therapeutic regimen comprises encapsulated Lenvatinib and Doxorubicin (Adriamycin™).

In another preferred embodiment, the embolizing particles or microspheres are DC Beads®, the encapsulating agents are DOTAP and DOPC and the therapeutic regimen comprises encapsulated Lenvatinib and Sunitinib (Sutent™).

In another preferred embodiment, the embolizing particles or microspheres are Oncozene™, the encapsulating agents are DOTAP and DOPC and the therapeutic regimen comprises encapsulated Sorafenib (Nexavar™) and Doxorubicin (Adriamycin).

In one preferred embodiment, the embolizing particles or microspheres are Oncozene™, the encapsulating agents are DOTAP and DOPC and the therapeutic regimen comprises encapsulated Sorafenib (Nexavar™) and Sunitinib (Sutent™).

In another preferred embodiment, the embolizing particles or microspheres are Oncozene™, the encapsulating agents are DOTAP and DOPC and the therapeutic regimen comprises encapsulated Regorafenib (Stivarga™) and Doxorubicin (Adriamycin™).

In another preferred embodiment, the embolizing particles or microspheres are Oncozene™, the encapsulating agents are DOTAP and DOPC and the therapeutic regimen comprises encapsulated Regorafenib (Stivarga™) and Sunitinib (Sutent™).

In another preferred embodiment, the embolizing particles or microspheres are Oncozene™, the encapsulating agents are DOTAP and DOPC and the therapeutic regimen comprises encapsulated Lenvatinib and Doxorubicin (Adriamycin™).

In another preferred embodiment, the embolizing particles or microspheres are Oncozene™, the encapsulating agents are DOTAP and DOPC and the therapeutic regimen comprises encapsulated Lenvatinib and Sunitinib (Sutent™).

In preferred embodiments for chemoembolization agents disclosed herein, compositions may include cholesterol in the range of 0-75%. In these embodiments, the liposome mixture may include 30-70% DOTAP and 30-70% DOPC. In some embodiments, the DOTAP and DOPC are present in an approximate 1:1 ratio. In some embodiments, the relative amount of DOTAP and DOPC ranges from, and includes 10-90% DOTAP and 10-90% DOPC. In some embodiments, the relative amount of DOTAP and DOPC ranges from, and includes 20-80% DOTAP and 20-80% DOPC. In some embodiments, the relative amount of DOTAP and DOPC ranges from, and includes 30-70% DOTAP and 30-70% DOPC. In some embodiments, the relative amount of DOTAP and DOPC ranges from, and includes 40-60% DOTAP and 40-60% DOPC.

2.4 Using the Compositions of the Disclosure.

Once prepared, the chemoembolization agents described herein are utilized in chemoembolization treatment of solid vascularized tumors. In some embodiments, methods developed for doxorubicin-loaded beads may be used for the selection of particle size, selection of proper dosage, the timing of treatments, methods of administration, and associated procedures such as imaging.

In some embodiments, chemoembolization agents are used in the treatment of any solid, vascularized tumor. In some embodiments, chemoembolization agents including Regorafenib are used in the treatment of HCC, tumors in the liver which have metastasized from other organs, metastatic colorectal cancers, or gastrointestinal stromal tumors. In some embodiments, chemoembolization agents including Sorafenib are used in the treatment of HCC, tumors in the liver which have metastasized from other organs, renal cell carcinoma, thyroid cancer, brain cancer, lung cancer, or desmoid tumors.

In some embodiments, the chemoembolization agents are combined with a tracer bead to enable tracking during the administration of the bead solution into the subject. In some embodiments, the tracer bead is radiopaque. In some embodiments, the radiopaque tracer bead is LC Bead Lumi (BTG, UK).

2.5 Combination Therapy

In some embodiments, chemoembolization may be used as the sole treatment or may be combined with other treatment options such as surgery (tumor resection), standard chemotherapy and/or radiotherapy. In some embodiments, chemoembolization can be applied before and/or after surgery (tumor resection), standard chemotherapy and/or radiotherapy.

The chemoembolization agents described herein may be administered as the sole pharmaceutical agent or in combination with one or more additional therapeutic agents. In some embodiments, the drug combination causes no unacceptable adverse effects. This combination therapy includes administration of a single pharmaceutical dosage formulation, which contains a chemoembolization agent described herein and one or more additional therapeutic agents in form of a single pharmaceutical composition, as well as administration of the chemoembolization agents described herein and each additional therapeutic agent in its own separate pharmaceutical dosage formulation, i.e. in its own separate pharmaceutical composition. For example, a chemoembolization agent described herein and another therapeutic agent may be administered to the patient together in a single oral dosage composition such as a tablet or capsule, or each agent may be administered in separate pharmaceutical compositions. Example therapeutic agents include but are not limited to Sorafenib, Regorafenib, Lenvatinib, Cabozantinib, Nivolumab, Pembrolizumab, Atezolizumab, Durvalumab, Avelumab, Ipilimumab or Tremelimumab.

Where separate pharmaceutical compositions are used, the chemoembolization agent and one or more other additional therapeutic agents may be administered at essentially the same time (for example, simultaneously), or at separately staggered times (for example, sequentially).

The term "standard chemotherapy" generally refers to a treatment of a cancer using specific chemotherapeutic/chemical agents. A chemotherapeutic agent refers to a pharmaceutical agent generally used for treating cancer. The chemotherapeutic agents for treating cancer interfering with DNA synthesis include, for example, cisplatin, carboplatin, etoposide, vincristine, cyclophosphamide, doxorubicin, ifosfamide, paclitaxel, gemcitabine, docetaxel, and irinotecan and platinum-based anti-cancer agents, including cisplatin and carboplatin. Other anti-cancer drugs include mitomycin C, tyrosine kinase inhibitors such as gefitinib, imatinib; farnesyl transferase inhibitors including lonafarnib; inhibitors of mammalian targets of rapamycin (mTOR) such as everolimus; inhibitors of PKC; PI3K and AKT.

The term "standard radiotherapy" refers to the use of ionizing radiation as part of cancer treatment to control malignant cells. Preferably the ionizing radiation is x rays or y-rays. It is also common to combine radiotherapy with surgery, chemotherapy, hormone therapy, or combinations thereof.

In some embodiments, the methods for the treatment of cancer described herein include the co-administration of radioembolization beads by transarterial radioembolization (TARE), also known as selective internal radiation therapy (SIRT), a procedure in which glass microspheres containing radioactive emitting ions are delivered to the tumor vasculature via transfemoral catheterization of the hepatic artery. The co-administration can be simultaneous or separate administration of the radioembolized beads and the chemoembolization agents described herein. In some embodiments, the radioembolization beads emit beta-radiation. In some embodiments, radioembolization beads includes a beta-radiation emitting ion selected from: Y-90, Sr-89, and Ra-223. In some embodiments, the radioembolization beads are TheraSphere Y-90 beads (ITG, UK).

2.6 Dosages

In some embodiments, dose of the administered chemoembolization agent is in the range of, including 0.1 to 500 mg per ml composition. In some embodiments, the dose of the administered chemoembolization agent is in the range of, including 10 to 100 mg per ml composition. In some embodiments, the treatment is repeated one to five times and for each dose the amount of therapeutic agent administered is in the range 0.1 to 100 mg per ml, preferably 10 to 100 mg per ml. In some embodiments, the amount of the chemoembolization agent composition administered in a normal treatment is in the range 1 to 6 ml. In some embodiments, the total amount of chemoembolization agent administered per dose is in the range of, including 0.01 mg to 1000 mg. In some embodiments, the total amount of chemoembolization agent administered per dose is in the range of, including, 25 to 250 mg. In some embodiments, the amount of chemoembolization agent administered per dose is 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000 mg.

In some embodiments, the amount of one or more therapeutic agents associated with an encapsulating agent is from 0.001 to 0.5 mg of therapeutic agent per mg of encapsulating agent. In some embodiments, the amount of one or more therapeutic agents associated with an encapsulating agent is 4.7229 mg of therapeutic agent per 201.1 mg of encapsulating agent.

However, as discussed herein, the adverse systemic side effects of therapeutic agent administration can be avoided by the localized administration of the chemoembolization agents.

The daily dose of the chemoembolization agents described herein will necessarily be varied depending upon the subject treated, the particular route of administration selected, and the severity and kind of the cancer being treated. Accordingly, the optimum dosage may be determined by the practitioner who is treating any particular subject. Further, the clinician or treating physician will know how and when to start, interrupt, adjust, or terminate therapy in conjunction with individual patient response. For any chemoembolization agent used in the method of the present description, a therapeutically effective dose can be estimated initially from cell culture assays, animal models, or micro-dosing of human subjects.

2.7 Kits

In some embodiments, this disclosure describes an article of manufacture having one or more of the chemoembolization agents described herein.

In some embodiments, the novel chemoembolization agents described herein are used as a pharmaceutical composition. The pharmaceutical compositions described herein may include at least one chemoembolization agent as described herein as an active ingredient together with at least one pharmaceutically acceptable (i.e. non-toxic) carrier, excipient and/or diluent. The pharmaceutical compositions as described herein can be prepared in a conventional solid or liquid carrier or diluent and a conventional pharmaceutically-made adjuvant at suitable dosage level in a known way.

EXAMPLES

Example 1. Sorafenib Encapsulation and Loading on DC Beads®

This was accomplished via a two-step process: 1) Sorafenib was made water-soluble by encapsulation into an encapsulating agent that is positively charged on its outer surface (cationic liposomes) and 2) association of a plurality of the loaded encapsulating agents so obtained onto microspheres (DC)Beads®. In order to accomplish this, Sorafenib para-toluene sulfonate salt (9.1 mg), DOTAP (1,2-dioleoyl-3-trimethylammonium-propane chloride salt, 100 mg) and DOPC (1,2-dioleoyl-sn-glycero-3-phosphocholine, 101.1 mg) were dissolved in ethanol (0.5 mL) and this solution was added dropwise to a 10% trehalose solution (9 mL) under stirring. The resulting viscous emulsion was stirred at room temperature for 5 minutes and then filtered through a manual liposomal extruder using a 200 nm polycarbonate membrane. The resulting unilamellar liposomal solution was lyophilized overnight to yield a white solid, which was reconstituted in deionized water (1.82 mL) to yield a final Sorafenib concentration of 5 mg/mL. DC Beads® (2 mL, having about 200,000 beads with an average bead diameter of about 100-300 microns as measured by light scattering) were drained of as much liquid as possible and treated with the liposomal solution. The concentration of Sorafenib in the supernatant was measured over time by HPLC/MS. After approximately 46 hours, equilibrium was reached and loading of Sorafenib appeared to be approximately 52%. It is possible that saturation was reached and that more beads are needed to increase loading. For elution experiments, the liposomal solution with the DC Beads® was passed through a cotton filter, leaving the DC beads® on the filter. PBS (1.0 M, pH 7.4) warmed to 37° C. was passed over the beads at 4 mL/min for 60 minutes. Four 40 mL vials were collected and analyzed by HPLC/MS/MS to determine the concentration of Sorafenib in each sample. Ten 3 mL vials were collected and analyzed by HPLC/MS/MS to establish the drug elution kinetics for Sorafenib.

Figure 15:
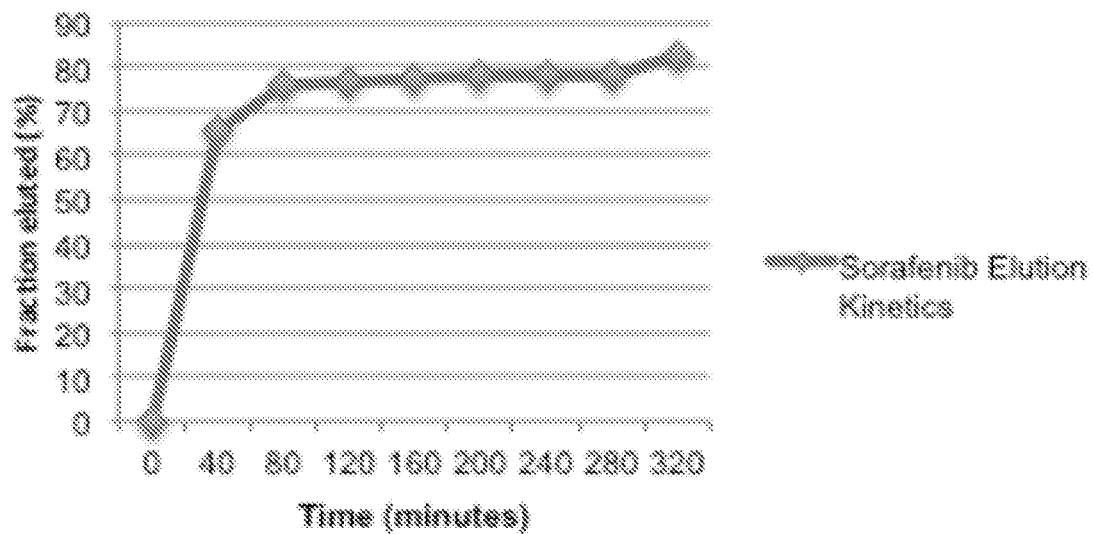
FIG. 15 is a graph showing the time course profile of elution of Sorafenib encapsulated in cationic liposomes and bound to DC Beads®.

FIG. 15 is a graph showing the fraction of Sorafenib eluted off the beads over time. After an initial larger release of Sorafenib from the beads, a constant flow of smaller but increasing amounts of drug were released over the time of the experiment. Approximately 17% of Sorafenib remained on the beads after the last elution time point. At the end, the beads were washed with dichloromethane to remove the remaining drug. These data suggest Sorafenib is released at high concentrations initially 4-20 µM and then in smaller increments (0.2 µM) thereafter (Table 1). All these concentrations approach or far exceed the cell based cytotoxic potency measured in vitro for HCC cells (Wilhelm S M, Carter C, Tang L, Wilkie D, McNabola A, Rong H, Chen C, Zhang X, Vincent P, McHugh M, Cao Y, Shujath J, Gawlak S, Eveleigh D, Rowley B, Liu L, Adnane L, Lynch M, Auclair D, Taylor I, Gedrich R, Voznesensky A, Riedl B, Post L E, Bollag G, Trail P A (2004) Cancer Res 64(19): 7099-109, which is incorporated herein by reference in its entirety). The human pharmacokinetics of Sorafenib given 400 mg twice daily (recommended therapeutic dose), shows mean t½ was 27.4 h and $C_{max}$ in plasma about 11.6 µM (Moore M, Hirte H W, Siu L, Oza A, Hotte S J, Petrenciuc O, Cihon F, Lathia C, Schwartz B (2005) Ann Oncol 16(10):1688-94, which is incorporated herein by reference in its entirety).

TABLE 1

Sorafenib elution kinetics from beads

| | amount loaded (mg) | | |
|---|---|---|---|
| start | 4.7229 | | |
| | Time (minutes) | amount eluted (mg) | % eluted | Cumulative elution % |
| Start | 0 | 0 | 0 | 0 |
| Fraction B | 40 | 3.09 | 65.4259 | 65.4259 |
| Fraction C | 80 | 0.504 | 10.6714 | 76.0973 |
| Fraction D | 120 | 0.0306 | 0.6479 | 76.7452 |
| Fraction E | 160 | 0.0327 | 0.6924 | 77.4376 |
| Fraction F | 200 | 0.00903 | 0.1912 | 77.6287 |
| Fraction G | 240 | 0.00561 | 0.11878 | 77.7475 |
| Fraction H | 280 | 0.000306 | 0.00648 | 77.754 |
| Fraction I (solvent - final) | 320 | 0.2328 | 4.9292 | 82.68317 |
| Remaining Sorafenib to be eluted | | 0.8179 mg | | |

Example 2. Regorafenib Encapsulation and Loading on DC Beads®

This was accomplished via a two-step process: 1) Regorafenib (4.7229 mg) was made water-soluble by encapsulation into an encapsulating agent that is positively charged on its outer surface (cationic liposomes) and 2) association of a plurality of the loaded encapsulating agents so obtained onto microspheres. In short, Regorafenib (6.9 mg), DOTAP (1,2-dioleoyl-3-trimethylammonium-propane chloride salt, 100 mg) and DOPC (1,2-dioleoyl-sn-glycero-3-phosphocholine, 101.1 mg) were dissolved in ethanol (0.5 mL) and this solution was added dropwise to a 10% trehalose solution (9 mL) under stirring. The resulting viscous emulsion was stirred at room temperature for 5 minutes and then filtered through a manual liposomal extruder using a 200 nm polycarbonate membrane. The resulting unilamellar liposomal solution was lyophilized overnight to yield a white solid, which was reconstituted in deionized water (1.8 mL) to yield a final Regorafenib concentration of 5 mg/mL. DC Beads® (2 mL) were drained of as much liquid as possible and treated with the liposomal solution. The concentration of Regorafenib in the supernatant was measured over time by HPLC/MS. After approximately 92 hours, equilibrium was reached and loading of Regorafenib appeared to be approximately 25%. For elution experiments, the liposomal solution with the DC Beads® was passed through a cotton filter, leaving the DC beads® on the filter. PBS (1.0 M, pH 7.4) warmed to 37° C. was passed over the beads at 4 mL/min for 60 minutes. Four 40 mL vials were collected and analyzed by HPLC/MS/MS to determine the concentration of Sorafenib in each sample.

Results

Figure 16:
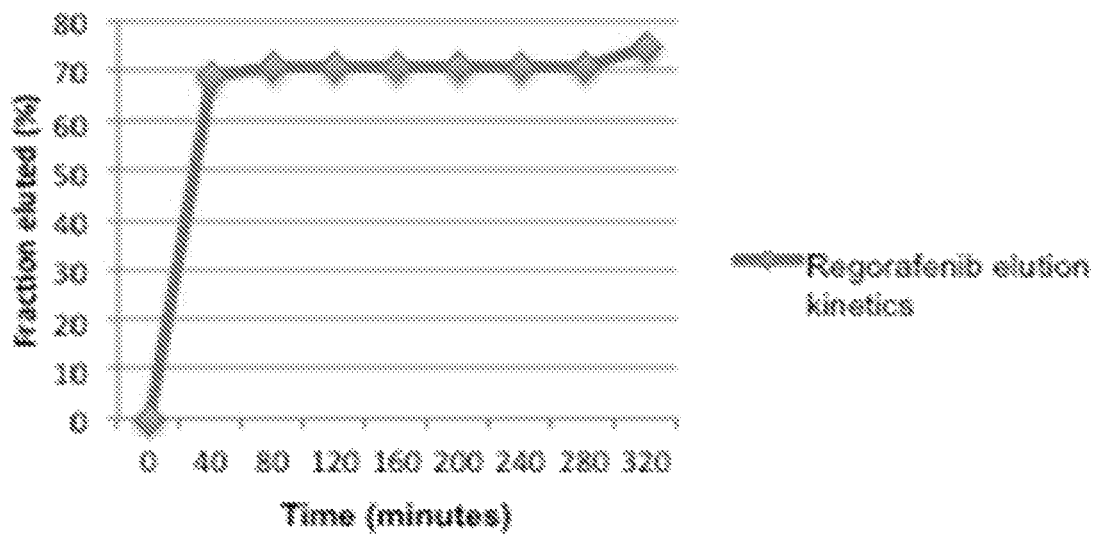
FIG. 16 is a graph showing the time course profile of elution of Regorafenib encapsulated in cationic liposomes and bound to DC Beads®.

Tables 1 and 2 show the concentration of Sorafenib and Regorafenib eluted from the DC Beads® over 40 minutes, respectively. FIGS. 15 and 16 show the cumulative concentration of Sorafenib and Regorafenib in each time point, respectively. For both Sorafenib and Regorafenib, after an initial larger release from the beads, smaller amounts of drug were released and appeared to reach equilibrium near the lower limit of quantitation (LLQ) for the MS/MS method. Only approximately 2% of the Sorafenib loaded was eluted over 40 minutes, and this result is in line with previous observations for doxorubicin, where only about 4% of doxorubicin was eluted after a 24 hour period.

TABLE 2

Regorafenib elution kinetics from beads

| | amount loaded (mg) | | |
|---|---|---|---|
| start | 2.1931 | | |

| | Time (minutes) | amount eluted (mg) | % eluted | Cumulative elution % |
|---|---|---|---|---|
| Start | 0 | 0 | 0 | 0 |
| Fraction B | 40 | 1.5 | 68.3963 | 68.3963 |
| Fraction C | 80 | 0.051 | 2.3255 | 70.7218 |
| Fraction C | 120 | 0.00024 | 0.0109 | 70.7327 |
| Fraction E | 160 | 0.0000628 | 0.00286 | 70.7356 |
| Fraction F | 200 | 0.0000372 | 0.0017 | 70.7373 |
| Fraction G | 240 | 0.0000364 | 0.0017 | 70.739 |
| Fraction H | 280 | 0.000108 | 0.0049 | 70.7439 |
| Fraction I (solvent - final) | 320 | 0.0776 | 3.5384 | 74.2823 |
| Remaining Regorafenib to be eluted | | 0.5723 mg | | |

The biocompatible PVA hydrogel beads 100-300 micron in diameter utilized in this study (DC Beads® 100-300 micrometers) are produced by BTG/Biocompatibles Inc. and commercialized as DC Beads®. The concentration of these beads solution (undiluted) is 200,000 beads per 2 ml of solution. These biocompatible beads are hydrophilic and require manipulation in aqueous medium. The beads have been modified with negatively charged alkyl sulfonate groups to allow ionic association with cationic encapsulating agents. The estimated pKa values for alkyl sulfonate groups is reported to be approximately 1.6 in DMSO and even lower in aqueous medium. For preparation of an embolization agent using PVA hydrogel beads as the embolizing microsphere without the benefit of an encapsulating agent, there are two requirements for successful loading of a therapeutic agent onto the microsphere: the therapeutic agent must be water-soluble at the concentrations >5 mg/mL, and the therapeutic agent must be sufficiently basic to allow efficient formation of an ion pair with the alkyl sulfonate groups on the polymeric bead. Sorafenib is mostly insoluble in water and essentially neutral (calculated pKa reported 2.03, ChemAxon).

Example 3. Tirapazamine Encapsulation and Loading on DC Beads®

Tirapazamine encapsulation and loading is accomplished according to a similar protocol as described in Examples 1 and 2.

Example 4. Therapeutic Regimen Comprising Sorafenib and Tirapazamine

Encapsulated samples of Sorafenib and Tirapazamine are prepared as described in Examples 1 and 3 and attached separately to DC Beads®. Loaded beads of each are combined via syringe to obtain the desired therapeutic regimen.

Example 5. Therapeutic Regimen Comprising Regorafenib and Tirapazamine

Encapsulated samples of Regorafenib and Tirapazamine are prepared as described in Examples 2 and 3 and attached separately to DC Beads®. Loaded beads of each are combined via syringe to obtain the desired therapeutic regimen.

Example 6: Doxorubicin Loading on DC Beads®

A drug-loading solution was prepared by adding sterile water to a vial of doxorubicin hydrochloride powder (Pharmacia & Upjohn, Kalamazoo, Mich.) to produce a solution of the desired concentration (for the loading experiment 25 mg Doxorubicin salt was dissolved in 5 mL water. 0.043 mmol/5 mL=8.6 mM solution). 1 mL volume of beads was aspirated via syringe, purged of as much liquid as possible, then an aqueous solution Doxorubicin (5 mL, 5 mg/mL concentration) aspirated and mixed with beads. The mixture was dispensed into a sealed vial and left to load at room temperature without agitation and left for a time until the red coloration in the solution had diminished and the beads had taken on a red color. This time was dependent on drug loading solution concentration and bead size.

The extent of drug loading was calculated from the residual unloaded drug content determined by UV/visible HPLC with DAD detector at 220 and 254 nm (Agilent 1100 Series). Estimated uptake of Doxorubicin was approximately 90% loading after 25 hours, and approximately 99% loading after 91 hours.

Example 7: Sunitinib Loading on DC Beads®

Sunitinib was loaded to DC beads® using a procedure similar to that for Example 6. Estimated uptake of Sunitinib was approximately 99% after 6 hours and >99.8% after 24 hours at room temperature.

Example 8. Therapeutic Regimen Comprising Sorafenib and Doxorubicin

Encapsulated samples of a Sorafenib solution and a Doxorubicin solution are prepared as described in Examples 1 and 6 and attached separately to DC Beads®. Loaded beads of each are combined via syringe to obtain the desired therapeutic regimen. A proportion of Sorafenib loaded beads/Doxorubicin loaded beads can be anywhere from 10:1 to 1:10, respectively. In some embodiments, the loading may be 3:1 to 1:3 or 2:1 to 1:2.

Example 9. Therapeutic Regimen Comprising Regorafenib and Doxorubicin

Encapsulated samples of a Regorafenib solution and a Doxorubicin solution are prepared as described in Examples 2 and 6 and attached separately to DC Beads®. Loaded beads of each are combined via syringe to obtain the desired therapeutic regimen. A proportion of Regorafenib loaded beads/Doxorubicin loaded beads can be anywhere from 10:1 to 1:10, respectively. In some embodiments, the loading may be 3:1 to 1:3 or 2:1 to 1:2.

Example 10. Therapeutic Regimen Comprising Sorafenib and Sunitinib

Encapsulated samples of a Sorafenib solution and a Sunitinib solution are prepared as described in Examples 1 and 7 and attached separately to DC Beads®. Loaded beads of each are combined via syringe to obtain the desired therapeutic regimen. A proportion of Sorafenib loaded beads/Sunitinib loaded beads can be anywhere from 10:1 to 1:10, respectively. In some embodiments, the loading may be 3:1 to 1:3 or 2:1 to 1:2.

Example 11. Therapeutic Regimen Comprising Regorafenib and Sunitinib

Encapsulated samples of a Regorafenib solution and a Sunitinib solution are prepared as described in Examples 2 and 7 and attached separately to DC Beads®. Loaded beads of each are combined via syringe to obtain the desired therapeutic regimen. A proportion of Regorafenib loaded beads/Sunitinib loaded beads can be anywhere from 10:1 to 1:10, respectively. In some embodiments, the loading may be 3:1 to 1:3 or 2:1 to 1:2.

Example 12. Sorafenib Encapsulation and Loading on Oncozene Beads™

Sorafenib encapsulation and loading is accomplished according to a similar protocol as described in Example 1 using Oncozene Beads™.

Example 13. Regorafenib Encapsulation and Loading on Oncozene Beads™

Regorafenib encapsulation and loading is accomplished according to a similar protocol as described in Example 2 using Oncozene Beads™.

Example 14. Tirapazamine Encapsulation and Loading on Oncozene Beads™

Tirapazamine encapsulation and loading is accomplished according to a similar protocol as described in Example 3 using Oncozene Beads™.

Example 15. Oncozene Chemoembolization Agent: Therapeutic Regimen Comprising Sorafenib and Tirapazamine Encapsulated samples of Sorafenib and Tirapazamine are prepared as described in Examples 1 and 3 and attached separately to Oncozene Beads™. Loaded beads of each are combined via syringe to obtain the desired therapeutic regimen. A proportion of Sorafenib loaded beads/Tirapazamine loaded beads can be anywhere from 10:1 to 1:10, respectively. In some embodiments, the loading may be 3:1 to 1:3 or 2:1 to 1:2.

Example 16. Oncozene Chemoembolization Agent: Therapeutic Regimen Comprising Regorafenib and Tirapazamine Encapsulated samples of Regorafenib and Tirapazamine are prepared as described in Examples 2 and 3 and attached separately to Oncozene Beads™. Loaded beads of each are combined via syringe to obtain the desired therapeutic regimen. A proportion of Regorafenib loaded beads/Tirapazamine loaded beads can be anywhere from 10:1 to 1:10, respectively. In some embodiments, the loading may be 3:1 to 1:3 or 2:1 to 1:2.

Example 17: Doxorubicin Loading on DC Beads®

Doxorubicin is loaded to Oncozene Beads™ using a procedure such as that provided in Example 6.

Example 18: Sunitinib Loading on DC Beads®

Sunitinib is loaded to Oncozene Beads™ using a procedure similar to that for Example 17.

Example 19. Oncozene™ Chemoembolization Agent: Therapeutic Regimen Comprising Sorafenib and Doxorubicin Encapsulated samples of a Sorafenib solution and a Doxorubicin solution are prepared as described in Examples 12 and 17 and attached separately to Oncozene Beads™. Loaded beads of each are combined via syringe to obtain the desired therapeutic regimen. A proportion of Sorafenib loaded beads/Doxorubicin loaded beads can be anywhere from 10:1 to 1:10, respectively. In some embodiments, the loading may be 3:1 to 1:3 or 2:1 to 1:2.

Example 20. Oncozene™ Chemoembolization Agent: Therapeutic Regimen Comprising Regorafenib and Doxorubicin Encapsulated samples of a Regorafenib solution and a Doxorubicin solution are prepared as described in Examples 13 and 17 and attached separately to Oncozene Beads™. Loaded beads of each are combined via syringe to obtain the desired therapeutic regimen. A proportion of Regorafenib loaded beads/Doxorubicin loaded beads can be anywhere from 10:1 to 1:10, respectively. In some embodiments, the loading may be 3:1 to 1:3 or 2:1 to 1:2.

Example 21. Oncozene™ Chemoembolization Agent: Therapeutic Regimen Comprising Sorafenib and Sunitinib Encapsulated samples of a Sorafenib solution and a Sunitinib solution are prepared as described in Examples 12 and 18 and attached separately to Oncozene Beads™. Loaded beads of each are combined via syringe to obtain the desired therapeutic regimen. A proportion of Sorafenib loaded beads/Sunitinib loaded beads can be anywhere from 10:1 to 1:10, respectively. In some embodiments, the loading may be 3:1 to 1:3 or 2:1 to 1:2.

Example 22. Oncozene™ Chemoembolization Agent: Therapeutic Regimen Comprising Regorafenib and Sunitinib Encapsulated samples of a Regorafenib solution and a Sunitinib solution are prepared as described in Examples 13 and 18 and attached separately to Oncozene Beads™. Loaded beads of each are combined via syringe to obtain the desired therapeutic regimen. A proportion of Regorafenib loaded beads/Sunitinib loaded beads can be anywhere from 10:1 to 1:10, respectively. In some embodiments, the loading may be 3:1 to 1:3 or 2:1 to 1:2.

Example 23. Treatment of Liver Cancer

The following example discloses treatment of liver cancer with chemoembolization agents.

The chemoembolization agents of Examples 1 or 2 is administered to a subject with liver cancer. Using imaging for guidance, a catheter is inserted up the femoral artery in the groin into the blood vessels supplying the liver tumor. The chemoembolization agent is injected into the catheter. The chemoembolization agent modulates blood flow to the tumor site as well as delivering chemotherapy agent directly to the tumor. One, two, three, four, five, six, seven, eight, nine, ten, eleven, or twelve applications are applied to treat the tumor. The use of chemoembolization agents as described herein results in reduced side effects than the systemic application of Sorafenib or Regorafenib. After thirty days, the subject's liver tumor size is reduced by 20-80% in total volume compared to the tumor size the day before administration of the chemoembolization agent. The use of chemoembolization agents as described herein also leads to increased reduction of the subject's liver tumor size when compared with embolization with beads alone.

Example 24. Animal Model and Tumor Implantation

The following describes testing in animal tumor model with chemoembolization agents.

The chemoembolization agents of Example 1 was tested for its drug release profiles, embolic properties and pharmacological efficacy in a rabbit liver cancer tumor model.

Adult New Zealand White rabbits weighing 3.6 to 4.1 kg were used. VX2 cell line was propagated and injected intramuscular into the hind limb of 3 donor rabbits. 23-25 days later animals were sacrificed, tumors were excised and used to supply tumor cells for surgical implantation into the liver of 10 recipient rabbits. The tumor suspension was inoculated via a sub-xyphoid midline incision into the left lateral lobe. Liver tumor developed in all animals without surgical complications.

Between 15-21 days after liver tumor implantation, in 10 rabbits (2 groups of 5 rabbits—9 and 18 mg Sorafenib), femoral artery was accessed through a surgical cut-down and catheterized with a 3 F vascular sheath, after which a 2 F micro catheter was advanced to the proper hepatic. Angiography was performed, tumor was visualized as a region of hyper vascular blush in the liver. The left hepatic artery was selectively catheterized off the common hepatic artery. DEE liposomal Sorafenib was then infused by hand under fluoroscopic visualization until vascular stasis was achieved. Post TACE, the femoral artery was ligated. Complete stasis was achieved by injecting 1.4 and 3.3 mg total Sorafenib concentration. Intra-arterial liposomal Sorafenib dosing was less than 1 mg/kg of animal weight. For pharmacokinetic measurement of systemic Sorafenib levels, blood samples were collected at selected time points following TACE (5 minutes, 1, 24 and 72 hours) before euthanizing the animals. Within 10 minutes of sacrifice, rabbit necropsy was performed and liver was harvested for tissue analysis. Treated tumors were extracted and divided in half for analysis. In addition, two representative 2 cm$^3$ samples of non-tumorous liver parenchyma—one from the left hepatic lobe and one from the right hepatic lobe—were also procured from each rabbit (three samples per animal, n=30).

Figure 17:
FIG. 17 is a photograph of a VX2 rabbit liver 72 hours after treatment with liposomal Sorafenib.
Figure 18:
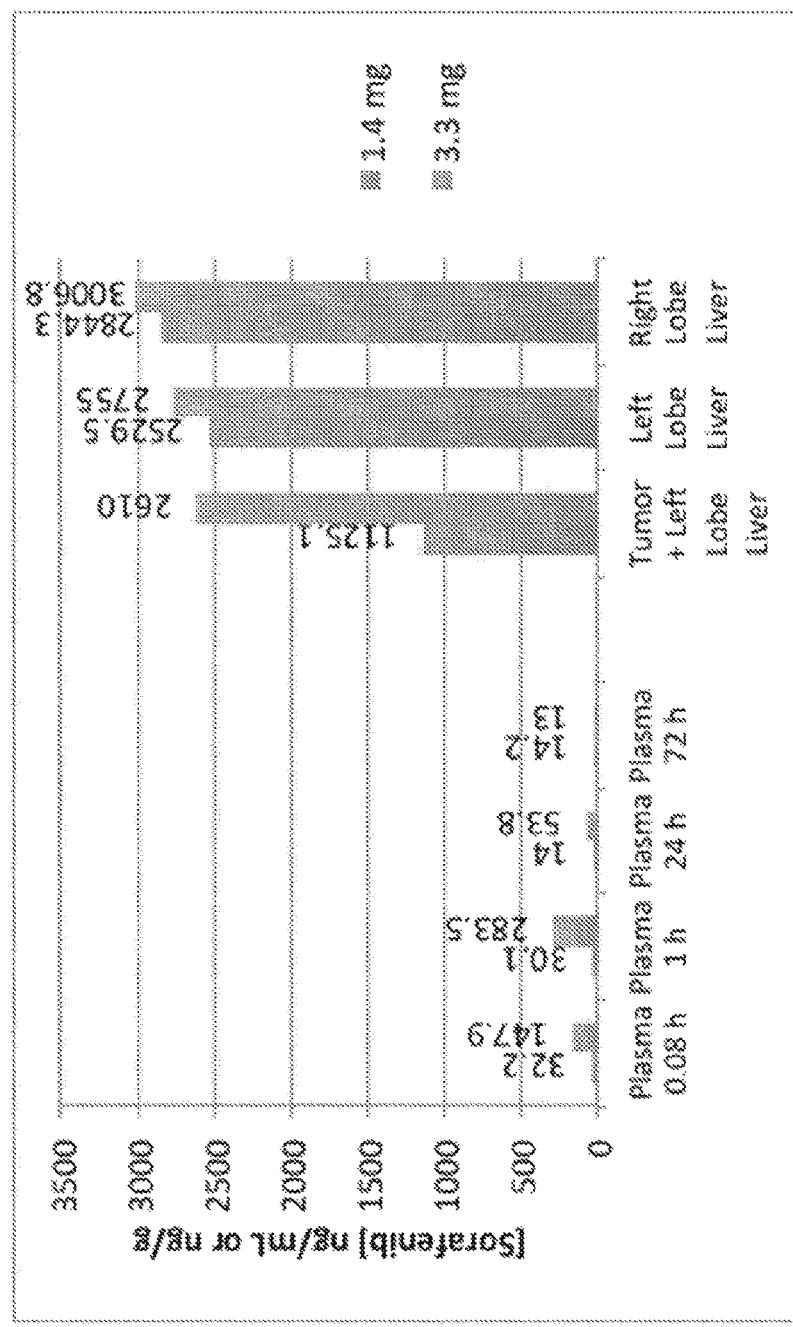
FIG. 18 is a graph showing plasma concentrations in a rabbit VX2 pharmacokinetic efficacy study.

As shown in FIG. 17, this Sorafenib delivery system appears sufficiently potent to induce gross tumor necrosis in this rabbit model. In this photograph, gross tumor necrosis is readily apparent. FIG. 18 shows liver tissue and plasma concentration of Sorafenib in each arm of the study. For each pair of bars on the graph, the bar on the reader's left represents mean values of rabbits treated with 1.4 mg Sorafenib formulation and the bar on the reader's right represents mean values of rabbits treated with 3.3 mg of Sorafenib formulation. Drug levels expressed in ng/g for liver tissue and ng/mL for plasma levels. The peak Sorafenib plasma concentration in the higher dose arm (3.3 mg) at 1 hour was 284 ng/mL, which is the equivalent of 0.61 µM, well below the $C_{max}$ achieved in humans. Conversely, the liver exposure of the high dose group was approximately 3,000 ng/g, over 10-fold the drug concentration in plasma. These results confirm our hypothesis and suggest that TACE with liposomal formulated Sorafenib reversibly linked to a DEE affords local delivery of an anti-VEGF agent with minimal systemic escape, and an apparent drug effect in the rabbit tumor model.

Example 25. Rabbit Liver Study

Multiple sections of each submitted liver tissue were evaluated. H&E slides were evaluated on low magnification (20×) for general assessment, distribution of percentage of necrosis or damage (if present), hepatocellular cytoplasmic degeneration and attributed zone followed by higher magnification assessment (100× and 400×). Trimming tissues: Each section was included normal and abnormal liver tissues, if present. If tumor was very large, representative of the tumor with adjacent grossly visible normal liver tissue or capsule were included. Grossly, two or more sections were examined from transverse and lateral planes.

A few notes regarding evaluation of the tissue samples: 1) viable tumor cells noticed at subcapsular and occasional fibrotic capsule areas of necrotic tumors; 2) very aggressive neoplasm with high mitotic figures and pleomorphic cells; and 3) severe hepatic damage even in non-affected lobes. Metastasis often observed on other lobes. The following abbreviations are used when describing the results: R: Right; L: Lobe or Left; NT: Non-tumor; T: Tumor; B: Blank; M: Medial, LLT: Left Lobe Tumor; P: letter observed on some sample tubes.

In Subject 1, sample RLP, the following was observed: zone 3 hepatocyte ballooning degeneration, mild, diffuse; rare foci of portal fibrosis with mild biliary hyperplasia; and rare foci of portal hepatitis, mixed to heterophilic, mild.

In Subject 1, sample LLT P, the following was observed: coagulative necrosis of tumor (>90%) and liver tissue with visible line of infarction; patchy areas of viable to semi-viable tumor cells noticed near zone of separation of intact and necrotic areas; dark basophilic globular materials noticed within arterial lumen of necrotic areas, multifocally; zone 3 hepatocyte ballooning degeneration, mild; and portal fibrosis with moderate to severe biliary hyperplasia in normal liver tissue adjacent to necrotic zone.

In Subject 1, sample LLNTP, the following was observed: large focally extensive acute hepatic necrosis with a clear line of infarction and heterophilic inflammation and necrosis; multifocal to coalescing acute liver necrosis with bridging pattern of normal liver issue adjacent to the infarcted area; involving zone 2 and 3 mainly; portal mixed and heterophilic inflammation is noticed with edema and fibrosis; and dark basophilic globular material noticed within arterial lumen of necrotic area, focal.

In Subject 2, sample LLNT, the following was observed: multifocal, randomly distributed foci of acute hepatic necrosis; portal fibrosis, mixed inflammation and mild biliary hyperplasia; dark basophilic globular material noticed within portal arterial lumen, multifocal; and zone 3 hepatocyte ballooning degeneration, moderate to severe.

In Subject 2, sample LLT, the following was observed: coagulative necrosis of entire tumor and associated liver tissue approximately; dark basophilic globular materials noticed within arterial lumen of necrotic areas, multifocally; and viable tumor cells noticed at overlying capsule and subcapsular area, focal.

In Subject 2, sample RL, the following was observed: multifocal, large foci of acute hepatic necrosis with line of demarcation/necrosis; portal fibrosis and mixed inflammation, multifocal; dark basophilic globular material noticed within portal arterial lumen of necrotic and nonnecrotic areas, multifocal; and metastatic vascular neoplastic foci noticed, multifocal.

In Subject 3, sample RL, the following was observed: multifocal, variably sized foci of acute hepatic necrosis, periportal and midzonal; portal fibrosis and mixed inflammation, multifocal; and dark basophilic globular material noticed within portal arterial lumen of non-necrotic areas, multifocal.

In Subject 3, sample LNT, the following was observed: few scattered small foci of acute hepatic necrosis (few cells) of ten periportal; portal hepatitis, mixed with edema; and zone 3 hepatocyte ballooning degeneration, mild.

In Subject 3, sample LLT, the following was observed: viable neoplasm involving approximately 20-25% of liver; foci of acute necrosis within center of neoplasm and neoplastic lobules; portal hepatitis, mixed with fibrosis, mild, multifocal.

In Subject 4, sample LLT, the following was observed: complete necrosis of neoplasm and associated liver tissue; rare foci of viable neoplastic cells observed in a subcapsular area; and dark basophilic globular material noticed within portal arterial lumen of necrotic areas, multifocal.

In Subject 4, sample LLNT, the following was observed: large focally extensive areas of acute hepatic necrosis with a clear line of infarction and heterophilic inflammation and necrosis; multifocal to coalescing acute liver necrosis with bridging pattern (zone 2 and 3) of normal liver issue adjacent to the infarcted areas; portal mixed and heterophilic inflammation is noticed with edema and fibrosis; and dark basophilic globular material noticed within arterial lumen of necrotic areas.

In Subject 4, sample RL, the following was observed: dark basophilic globular material noticed within portal arterial lumen with thrombosis; and zone 3 hepatocyte ballooning degeneration, mild.

In Subject 5, sample LLT, the following was observed: viable tumor cells involving approximately 80% of liver parenchyma invading into muscle fibers; metastatic neoplasm in portal vessels of normal liver parenchyma with portal fibrosis; larger areas of coagulation necrosis within center of neoplastic lobules/parenchyma; and dark basophilic globular materials noticed within portal vascular lumen of normal and neoplastic liver.

In Subject 5, sample RL, the following was observed: few portal triads, non-heterophilic inflammatory cell infiltrate, mild.

In Subject 5, sample LLNT, the following was observed: viable tumor cells involving approximately 70% of liver parenchyma; metastatic neoplasm in portal vessels of normal liver parenchyma; areas of coagulation necrosis within center of neoplastic lobules/parenchyma; and dark basophilic globular materials noticed within portal vascular lumen of normal and neoplastic liver.

In Subject 6, sample LLNTP, the following was observed: appears to be diffuse postmortem autolytic changes of hepatocytes with karyorrhexis and karyolysis; and rare scattered small foci of heterophilic hepatic necrosis.

In Subject 6, sample RLP, the following was observed: mixed to heterophilic portal hepatitis with portal fibrosis and various biliary hyperplasia; acute hepatic necrosis, multifocal, peri-portal and midzonal with heterophilic inflammation; and dark basophilic globular materials noticed within portal vascular lumen with thrombosis.

In Subject 6, sample LLTP, the following was observed: massive coagulative necrosis of tumor parenchyma and associated liver tissue >90%; viable tumor cells noticed at periphery of tissue and cut margins; dark basophilic globular materials noticed within vascular lumen of normal and neoplastic liver; and distorted normal adjacent liver parenchyma with mixed inflammation within sinusoids.

In Subject 7, sample LLT, the following was observed: multifocal large neoplastic foci affecting approximately 70-80% of the liver parenchyma; areas of lytic and coagulative necrosis with the tumor areas; and portal fibrosis, mild with edema and rare biliary hyperplasia and lymphocytic inflammation.

In Subject 7, sample LLNT, the following was observed: portal hepatitis, mild, lymphoplasmacytic with rare heterophils.

In Subject 7, sample RL. The following was observed: dark basophilic globular materials noticed within vascular lumen of few portal areas with edema; portal hepatitis, mild, multifocal, mixed inflammatory cells; hepatocellular cytoplasmic vacuolar degenerative changes, moderate to severe; and few dilated central veins with luminal thrombus.

In Subject 8, sample RL, the following was observed: hepatocellular cytoplasmic vacuolar degenerative changes, mild to moderate, zone 3-Portal hepatitis, mild, multifocal, mostly lymphoplasmacytic.

In Subject 8, sample LLT, the following was observed: multifocal neoplastic foci affecting approximately 20% of the liver parenchyma; areas of lytic and coagulative necrosis within the tumor parenchyma; capsular fibrosis associated with the neoplastic areas; and hepatocellular cytoplasmic vacuolar degenerative changes, moderate, zone 3.

In Subject 9, sample LLNTP, the following was observed: neoplastic foci at the margin of the section with desmoplasia and peripheral necrosis; areas of lytic and coagulative necrosis within the tumor parenchyma and viable cells at the periphery; and hepatocellular cytoplasmic vacuolar degenerative changes, mild, zone 3.

In Subject 9, sample LLTP, the following was observed: massive obliteration of liver parenchyma by neoplastic foci affecting approximately 80%; areas of lytic and coagulative necrosis within the tumor lobules and viable cells at the periphery; and hepatocellular cytoplasmic vacuolar degenerative changes, mild, zone 3.

In Subject 9, sample RLP, the following was observed: hepatocellular cytoplasmic vacuolar degenerative changes, severe, zone 3.

In Subject 10, sample T, the following was observed: tissue appears not fixed properly in formalin (leaked formalin noticed on gross examination); histologically, there is severe and diffuse postmortem autolytic changes of hepatocytes; few bacteria seen at the edge of tissue; and no histologic neoplastic changes noticed.

In Subject 10, sample BNT, the following was observed: obliteration of liver parenchyma by neoplastic foci affecting approximately 40% of liver tissue; there is severe and diffuse postmortem autolytic changes of normal hepatocytes; and many postmortem bacterial colonies seen within the liver tissue.

In Subject 11, sample T, the following was observed: multifocal neoplastic foci affecting approximately 30% of the liver parenchyma with desmoplasia; areas of lytic and coagulative necrosis within the tumor lobules; capsular and subcapsular neoplastic foci with necrosis (possible intraabdominal metastasis); and hepatocellular cytoplasmic vacuolar degenerative changes, mild, zone 3.

In Subject 11, sample RL, the following was observed: hepatocellular cytoplasmic vacuolar degenerative changes, mild, zone 2 and 3.

In Subject 12, sample LLNT, the following was observed: few small foci of neoplasms observed in parenchyma and in vascular lumen of portal area; and hepatocellular cytoplasmic vacuolar degenerative changes, moderate, zone 3.

In Subject 12, sample RL, the following was observed: multifocal to coalescing foci of acute hepatic necrosis; hepatocellular cytoplasmic vacuolar degenerative changes, severe, zone 2 and 3; and one dark basophilic globular material noticed in a portal area with heterophilic portal inflammation.

In Subject 12, sample RLT, the following was observed: large neoplasm involving 30% of liver with complete necrosis of neoplasm; thin rim of viable neoplastic cells observed in subcapsular area and one focus in the normal liver parenchyma; acute hepatic necrosis, focally extensive (infarction); and dark basophilic globular material noticed within necrotic area of neoplasm, multifocal.

In Subject 12, sample LM, the following was observed: massive, focally extensive, acute, coagulative hepatic necrosis.

In Subject 13, sample LLT, the following was observed: large neoplastic foci affecting approximately 30% of the liver parenchyma with desmoplasia; areas of lytic and coagulative necrosis within central tumor lobules; and dark basophilic globular materials noticed in a portal areas of peripheral normal liver.

In Subject 13, sample RL, the following was observed: few multifocal heterophilic portal inflammation, mild to moderate.

In Subject 13, sample LLNT, the following was observed: few multifocal heterophilic portal inflammation, mild to moderate; dark basophilic globular materials noticed in few portal areas; and hepatocellular cytoplasmic vacuolar degenerative changes, mild, zone 3.

Example 26. Preparation of Liposomes Containing Sorafenib 1,2 dioleoyl-3-trimethylammoniumpropane (DOTAP) and 1,2 dioleoyl-sn-glycero3-phosphocholine (DOPC) (Avanti Polar Lipids Inc. Alabaster, Ala., USA) are used for preparation of cationic liposomes. Liposome production is performed on the basis of standard procedures as described in the literature (Chang H I, Cheng M Y, Yeh M K (2012) Clinically-Proven Liposome-Based Drug Delivery: Formulation, Characterization and Therapeutic Efficacy. 1: 195. doi:10.4172/scientificreports.195 and Chang H I, Yeh M K (2012). Clinical development of liposome-based drugs: formulation, characterization, and therapeutic efficacy. Int J Nanomedicine 7:49-60, which are herein incorporated by reference in the entirety). To accomplish this, DOTAP, DOPC and Sorafenib are dissolved in ethanol in a molar ratio of 50/45/5. The concentrated ethanol solution is injected under stirring into a 10% trehalose solution to obtain a suspension of multilamellar liposomes. These are extruded through polycarbonate membranes, pore size 200 nm and the resulting monodisperse monolamellar liposomes are sterile filtered using MilliPak filters, 220 nm. The liposomes are filled in glass vials and lyophilized. The lyophilized liposomal Sorafenib is resuspended in water for DEE loading experiments.

Example 27. Release Profile Study

Studies are conducted to characterize a suitable release profile for Sorafenib formulations for evaluation in preclinical studies. To accomplish this, a volume of 1 mL of beads is aspirated via syringe and purged of the supernatant. One mL of formulated Sorafenib or (5 mg/mL) is aspirated and mixed with beads. The mixture is dispensed into a sealed vial and left to load at room temperature without agitation. Ten µL of the supernatant is sampled and diluted with 90 µL water for HPLC/MS injection at various time points. Elution experiments are conducted according to methods described in the preliminary results section and the literature (Lewis A L, Gonzalez M V, Lloyd A W, Hall B, Tang Y, Willis S L, Leppard S W, Wolfenden L C, Palmer R R, Stratford P W (2006). DC bead: in vitro characterization of a drug-delivery device for transarterial chemoembolization. J Vasc Interv Radiol 17(2 Pt 1):335-42, which is incorporated herein by reference in its entirety).

Example 28. Evaluation of In Vitro Efficacy of Sorafenib Formulation in HCC Cells Sorafenib formulations are assessed for their level of cytostatic action on HCC cells to demonstrate proof of biological efficacy in vitro. MTT cell proliferation assays: HepG2 and SMMC7721 cells are used for this study. Cells ($5\times10^3$) are cultured in 96-well flat-bottomed plates. Cells are cultured in 100 µL DMEM containing 10% FBS and 20 µL MTS reagent powder (Promega, Madison, Wis., USA). Cells are harvested and seeded on 96-well flat-bottomed plates, which are incubated at 37° C. for 4 h. After incubation for 1, 2, 3, 4, or 5 days, the absorbance at 550 nM is determined for each well. The growth inhibition activity is assessed as described previously, according to the slightly modified procedure of the National Cancer Institute, Developmental Therapeutics Program (Boyd, M. R.; Kenneth, D. P (1995). Some practical considerations and applications of the National Cancer Institute in vitro anticancer drug discovery screen. Drug Dev. Res 34, 91-109, which is incorporated herein by reference in its entirety). Tested agents are then added in five consecutive 10-fold dilutions (10-8 to 10-4 mol·L$^{-1}$) and incubated for further 72 h. The solvent (DMSO) is also tested for eventual inhibitory activity by adjusting its concentration to be the same as in working concentrations (maximal concentration of DMSO is 0.25%). After 72 h of incubation, the cell growth rate is evaluated by performing the MTT assay (Promega) which detects dehydrogenase activity in viable cells. The results are expressed as $IC_{50}$, which is the concentration necessary for 50% of inhibition. The $IC_{50}$ values for each compound are calculated from dose-response curves using linear regression analysis.

Example 29. Evaluation of In Vivo Efficacy of Sorafenib in a Multi-Arm Rabbit Tumor Model Sorafenib formulations are tested for their drug release profiles, embolic properties and pharmacological efficacy in a VX2 rabbit tumor model of HCC (Rao P P, Pascale F, Seck A, Auperin A, Drouard-Troalen L, Deschamps F, Teriitheau C, Paci A, Denys A, Bize P, de Baere T (2012). Irinotecan loaded in eluting beads: preclinical assessment in a rabbit VX2 liver tumor model. Cardiovasc Intervent Radiol. 35(6): 1448-59 and Hong K, Khwaja A, Liapi E, Torbenson M S, Georgiades C S, Geschwind J F (2006). New intra-arterial drug delivery system for the treatment of liver cancer: preclinical assessment in a rabbit model of liver cancer. Clin Cancer Res. 12(8):2563-7, which are herein incorporated by reference in the entirety). Treated animals will be evaluated to verify that i) Sorafenib is released into the local environment, ii) drug release is local to the liver with minimal systemic exposure and iii) Sorafenib/DEE is efficacious in a tumor model. Arm 1 of the study is DEE with fast elution profile, arm 2 is Sorafenib loaded DEE with a slower release profile, arm 3 is Doxorubicin loaded DEE, arm 4 is embolics alone with IA delivered Sorafenib, and arm 5 is systemic Sorafenib. Each arm uses at least 3 rabbits for the study, 3 rabbits are used as donors and 3 rabbits for attrition. Total of 45 rabbits.

Methods: An established rabbit liver cancer model is utilized (Cardiovasc Intervent Radiol. 35(6):1448-59 and Clin Cancer Res. 12(8):2563-7). VX2 tumors are initially established in the hind leg of adult New Zealand rabbits. Tumors are then harvested and implanted in the left lobe of the liver of two different rabbits during exploratory laparotomy under general anesthesia. Confirmation of tumor development is performed at 10-14 days by abdominal ultrasound. Once the tumors reach 2.5 to 3.5 cm they are treated. Under general anesthesia and fluoroscopy the left hepatic artery are cannulated via a femoral artery approach. Sorafenib or doxorubicin/DEE beads are delivered—one vial or until stasis is obtained (whichever comes first). Analgesic buprenorphine (0.02-0.05 mg/kg) is administered post procedure(s) for pain and distress. Animals are then humanely euthanized and blood and tissue are collected to quantify levels of Sorafenib.

Example 30. Determination of Drug Levels

Sorafenib or Regorafenib plasma levels are measured immediately at the end of the embolization procedure. Whole blood samples are collected into potassium ethylenediamine tetraacetic acid tubes and centrifuged. Plasma samples are stored at −20° C. until analysis by liquid chromatography—tandem mass spectrometry. Measurements of Sorafenib or Regorafenib are performed in four tissue samples per animal to limit sampling errors (two in the right lobe and two in the left lobe), using the same mass spectrometry method after sacrifice.

All patents, patent applications, and publications cited in this specification are incorporated by reference herein to the same extent as if each independent patent application or publication was specifically and individually indicated to be incorporated by reference. The disclosed embodiments are presented for purposes of illustration and not limitation. While chemoembolization agents have been described with reference to the described embodiments thereof, it will be appreciated by those of skill in the art that modifications can be made to the structure and elements of the chemoembolization agents without departing from the spirit and scope of the description as a whole.

The foregoing description details certain embodiments of the compositions and methods disclosed herein. It will be appreciated, however, that no matter how detailed the foregoing appears in text, the compositions and methods can be practiced in many ways. As is also stated above, it should be noted that the use of particular terminology when describing certain features or aspects of the chemoembolization agents should not be taken to imply that the terminology is being re-defined herein to be restricted to including any specific characteristics of the features or aspects of the technology with which that terminology is associated.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment may be interchangeable with other embodiments; one or more parts from a depicted embodiment can be included with other depicted embodiments in any combination. For example, any of the various components described herein and/or depicted in the Figures may be combined, interchanged or excluded from other embodiments. The above description discloses several compositions, methods and materials of the chemoembolization agents. The chemoembolization agents are susceptible to modifications in the compositions, methods and materials, as well as alterations in the fabrication methods and equipment. Such modifications will become apparent to those skilled in the art from a consideration of this disclosure or practice of the chemoembolization agents described herein. Consequently, it is not intended that chemoembolization agents be limited to the specific embodiments described herein, but that it cover all modifications and alternatives coming within the true scope and spirit of the chemoembolization agents as embodied in the attached claims. Applicant reserves the right to submit claims directed to combinations and sub-combinations of the described chemoembolization agents that are believed to be novel and non-obvious. chemoembolization agents embodied in other combinations and sub-combinations of features, functions, elements and/or properties may be claimed through amendment of those claims or presentation of new claims in the present application or in a related application. Such amended or new claims, whether they are directed to the same chemoembolization agents or different chemoembolization agents and whether they are different, broader, narrower or equal in scope to the original claims, are to be considered within the subject matter of the chemoembolization agents described herein.

What is claimed is:

1. A chemoembolization agent, comprising:
an embolizing particle or microsphere;
an encapsulating agent, the encapsulating agent being affixed to the embolizing particle or microsphere through ionic or other non-covalent interactions,
one or more therapeutic agents contained within the encapsulating agent,
wherein each therapeutic agent is independently uncharged or weakly charged or has low solubility in aqueous media at physiological pH; and
wherein the encapsulating agent is configured to release the one or more therapeutic agents.

2. The chemoembolization agent of claim 1, wherein each therapeutic agent is independently an anti-cancer agent.

3. The chemoembolization agent of claim 2, wherein the chemoembolization agent is comprised of one anti-cancer agent contained within the encapsulating agent, wherein the one anti-cancer agent is selected from the group consisting of Sorafenib, Regorafenib, Lenvatinib, Tirapazamine, Cabozantinib, and Sunitinib.

4. The chemoembolization agent of claim 3, wherein the one anti-cancer agent is Sorafenib, Regorafenib, or Lenvatinib.

5. The chemoembolization agent of claim 1 further comprising a non-encapsulated therapeutic agent affixed via a releasable mechanism to the embolizing particle or microsphere.

6. The chemoembolization agent of claim 1, wherein the embolizing particle or microsphere is a polyvinyl alcohol material.

7. The chemoembolization agent of claim 6, wherein the embolizing particle or microsphere is selected from the group consisting of beads of sulfonate functionalized polyvinyl alcohol hydrogels, acetalized polyvinyl alcohol hydrogels, polyvinyl alcohol hydrogel cores made of sodium poly (methacrylate) coated with poly bis[trifluoroethoxy]phosphazene, and polyvinyl alcohol-co-sodium acrylate cross-linked hydrogels, and hydrogel networks of poly ethylene glycol and 3-sulfopropyl acrylate.

8. The chemoembolization agent of claim 1, wherein the encapsulating agent is a liposome.

9. The chemoembolization agent of claim 1, wherein the liposome is a cationic liposome.

10. The chemoembolization agent of claim 9, wherein the cationic liposome comprises a mixture of DOTAP and DOPC.

11. The chemoembolization agent of claim 10, wherein the molar ratio of DOTAP to DOPC ranges from 1:9 to 9:1.

12. A pharmaceutical composition comprising a therapeutically effective amount of the chemoembolization agent of claim 9 and at least one pharmaceutically acceptable excipient.

* * * * *

UNITED STATES PATENT AND TRADEMARK OFFICE
CERTIFICATE OF CORRECTION

| | | |
|---|---|---|
| PATENT NO. | : 11,712,418 B2 | Page 1 of 1 |
| APPLICATION NO. | : 16/616808 | |
| DATED | : August 1, 2023 | |
| INVENTOR(S) | : James Na et al. | |

It is certified that error appears in the above-identified patent and that said Letters Patent is hereby corrected as shown below:

In the Claims

Column 42, Line 15, Claim 9:
After "The chemoembolization agent of claim"
Delete "1" and
Insert -- 8 --.

Signed and Sealed this
Twenty-second Day of October, 2024

Katherine Kelly Vidal
*Director of the United States Patent and Trademark Office*